(12) United States Patent  
Fujimori et al.

(10) Patent No.: US 7,775,971 B2  
(45) Date of Patent: Aug. 17, 2010

(54) CAPSULE APPARATUS WITH RIGID AND FLEXIBLE WIRING BOARD SECTIONS

(75) Inventors: Noriyuki Fujimori, Nagano (JP); Hiroshi Suzushima, Nagano (JP)

(73) Assignee: Olympus Corporation, Tokyo (JP)

( * ) Notice: Subject to any disclaimer, the term of this patent is extended or adjusted under 35 U.S.C. 154(b) by 1061 days.

(21) Appl. No.: 11/488,336

(22) Filed: Jul. 18, 2006

(65) Prior Publication Data

US 2006/0264704 A1 Nov. 23, 2006

Related U.S. Application Data

(63) Continuation of application No. PCT/JP2005/000490, filed on Jan. 17, 2005.

(30) Foreign Application Priority Data

Jan. 19, 2004 (JP) ............................... 2004-010713  
Jan. 22, 2004 (JP) ............................... 2004-041623

(51) Int. Cl.
 *A61B 1/00* (2006.01)
 *A61B 1/04* (2006.01)
 *A61B 1/06* (2006.01)
(52) U.S. Cl. .................. 600/110; 600/130; 600/160
(58) Field of Classification Search .................. 600/109, 600/110, 130, 160, 476, 407, 302; 348/76
 See application file for complete search history.

(56) References Cited

U.S. PATENT DOCUMENTS

| | | | | |
|---|---|---|---|---|
| 4,895,138 A | * | 1/1990 | Yabe ............................. | 600/110 |
| 4,993,405 A | * | 2/1991 | Takamura et al. ............ | 600/110 |
| 5,427,087 A | * | 6/1995 | Ito et al. ....................... | 600/109 |
| 5,857,963 A | * | 1/1999 | Pelchy et al. ................. | 600/109 |
| 6,142,930 A | * | 11/2000 | Ito et al. ....................... | 600/109 |
| 6,313,456 B1 | | 11/2001 | Miyashita et al. | |
| 2002/0103417 A1 | * | 8/2002 | Gazdzinski ................... | 600/109 |
| 2004/0171914 A1 | * | 9/2004 | Avni ............................. | 600/160 |

(Continued)

FOREIGN PATENT DOCUMENTS

EP 1 342 447 A2 9/2003

(Continued)

OTHER PUBLICATIONS

Japanese Office Action dated Jul. 24, 2007.

(Continued)

*Primary Examiner*—John P Leubecker  
(74) *Attorney, Agent, or Firm*—Scully, Scott, Murphy & Presser, P.C.

(57) ABSTRACT

An capsule-type medical apparatus includes a sealed container; and a wiring board which is housed in the sealed container and on which a functional circuit performing a predetermined function while the capsule-type medical apparatus is inserted into a subject is mounted. The wiring board includes a plurality of comparatively rigid wiring board sections on which parts constituting the functional circuit are mounted, and a comparatively flexible wiring board section that connects the plurality of the rigid wiring board sections. The flexible wiring board is extended from a straight-line portion formed on the rigid wiring board sections, and the flexible wiring board section is folded so that the adjacent rigid wiring board sections oppose to each other.

6 Claims, 18 Drawing Sheets

U.S. PATENT DOCUMENTS

| | | | |
|---|---|---|---|
| 2005/0049461 A1* | 3/2005 | Honda et al. | 600/160 |
| 2006/0004257 A1* | 1/2006 | Gilad et al. | 600/160 |
| 2006/0004276 A1* | 1/2006 | Iddan et al. | 600/407 |
| 2006/0015013 A1* | 1/2006 | Gilad et al. | 600/160 |
| 2006/0100496 A1* | 5/2006 | Avron | 600/407 |
| 2006/0104057 A1* | 5/2006 | Avron et al. | 362/227 |
| 2006/0149132 A1* | 7/2006 | Iddan | 600/160 |
| 2007/0219435 A1* | 9/2007 | Segawa et al. | 600/302 |

FOREIGN PATENT DOCUMENTS

| | | |
|---|---|---|
| JP | 11-289141 | 10/1999 |
| JP | 2000-083252 | 3/2000 |
| JP | 2001-091860 | 4/2001 |
| JP | 2001-112709 | 4/2001 |
| JP | 2001-112710 | 4/2001 |
| JP | 2001-231744 | 8/2001 |
| JP | 2003-210394 | 7/2003 |
| JP | 2003-210395 | 7/2003 |
| JP | 2003-260023 | 9/2003 |
| JP | 2003-260024 | 9/2003 |
| JP | 2003-325441 | 11/2003 |
| WO | WO 02/102224 A2 | 12/2002 |

OTHER PUBLICATIONS

Japanese Office Action dated Aug. 21, 2007.

* cited by examiner

CAPSULE APPARATUS WITH RIGID AND FLEXIBLE WIRING BOARD SECTIONS

CROSS-REFERENCE TO RELATED APPLICATIONS

This application is a continuation of PCT international application Ser. No. PCT/JP2005/000490 filed Jan. 17, 2005 which designates the United States, incorporated herein by reference, and which claims the benefit of priority from Japanese Patent Applications No. 2004-010713, filed Jan. 19, 2004; and No. 2004-014623, filed Jan. 22, 2004, both incorporated herein by reference.

BACKGROUND OF THE INVENTION

1. Field of the Invention

The present invention relates to an capsule-type medical apparatus that houses a wiring board, on which a functional circuit is mounted, in a sealed container. The capsule-type medical apparatus performs a predetermined function by driving of the functional circuit while the capsule-type medical apparatus is put in a subject.

2. Description of the Related Art

A capsule-type medical apparatus, which has a capsule-like shape and is capable of acquiring information such as a pH value and a temperature inside a subject, makes an appearance in recent years. In a field of endoscope, the capsule endoscope is now attracting attention together with a conventional endoscope, for the reason that the capsule endoscope can relieve suffering of a subject, for example.

The capsule endoscope houses, for example, a power supply 3 and a wiring board 2 consisting of a functional circuit inside a capsule-shaped sealed container 1 in order to acquire image data inside a body cavity while the capsule endoscope is inserted into the body cavity of the subject, as shown in FIG. 20. The sealed container 1 is provided with a container main body 1*a* having a cylindrical shape and having a bottom, as well as provided with a front cover 1*b* formed of an optical material. The sealed container is configured by attaching the front cover 1*b* to a distal end of the container main body 1*a* while keeping a desired water-tightness therebetween, after housing the wiring board 2 and the power supply 3 inside the container main body 1*a*. The sealed container 1 has a size swallowable by a human being, and both ends thereof are each formed in semi-spherical shape. Various functional parts and electronic parts such as an illumination unit 4, a lens unit 5, an imaging element 6, and a radio transmission unit 7 are mounted on the wiring board 2 to form the functional circuit described above.

In order to use the capsule endoscope, the capsule endoscope is swallowed by the subject while the power supply 3 is turned on. When the capsule endoscope is inserted into the body cavity of the subject, the illumination unit 4 illuminates the inside of the subject body such as an observed region of stomach, small intestine, and large intestine with an illuminating light through the front cover 1*b* until the capsule endoscope is discharged from the subject body. Then, an image is formed on an imaging element 6 through the lens unit 5 by an incident reflective light through the front cover 1*b*. Consequently, the image formed on the imaging element 6 by the reflective light is output as an image signal. Further, the image signal output from the imaging element 6 is radio transmitted outside by the radio transmission unit 7, and a receiver arranged outside the subject body receives the image data, thereby allowing for observation of the data (for example, see JP-A 2001-91860 (KOKAI) and International Publication WO 02/102224).

In the capsule endoscope described above, a plurality of circular circuit board sections 2*a* and a strip-shaped connection strip board section 2*b* that is arranged between the circular circuit board sections 2*a*, which are integrally formed, constitute the wiring board 2 as shown in FIG. 21. The functional parts and the electronic parts are effectively housed in the sealed container 1 by housing the circular circuit board sections 2*a* and the connection strip board section 2*b* in the sealed container 1 while folding the connection strip board section 2*b* so that the circular circuit board sections 2*a* are located in parallel with each other.

However, it is difficult to fix a position to be folded on the wiring board 2 consisting of the circular circuit board sections 2*a* and the connection strip board sections 2*b* which are integrally formed. For example, the connection strip board section 2*b* may be folded at a position apart from the circular circuit board section 2*a*, or the connection strip board section 2*b* may be folded obliquely with respect to a tangential direction of the circular circuit board section 2*a*.

An outside dimension of the wiring board 2 folded at the position apart from the circular circuit board section 2*a* or folded obliquely with respect to the tangential direction of the circular circuit board section 2*a* may become larger than the inner diameter of the sealed container 1, so that assembly operation such as insertion of the circuit board 2 into the sealed container 1 becomes complicated. As a matter of course, if the sealed container 1 is sufficiently-large, then the inconvenience described above can be avoided. However, it becomes complicated to insert the large sealed container 1 into the subject body. Such inconvenience, but not limited to the capsule endoscope, is common for various capsule-type medical apparatuses.

SUMMARY OF THE INVENTION

An capsule-type medical apparatus according to one aspect of the present invention includes a sealed container; and a wiring board which is housed in the sealed container and on which a functional circuit performing a predetermined function while the capsule-type medical apparatus is inserted into a subject is mounted. The wiring board includes a plurality of comparatively rigid wiring board sections on which parts constituting the functional circuit are mounted, and a comparatively flexible wiring board section that connects the plurality of the rigid wiring board sections. The flexible wiring board is extended from a straight-line portion formed on the rigid wiring board sections, and the flexible wiring board section is folded so that the adjacent rigid wiring board sections oppose to each other.

An capsule-type medical apparatus according to another aspect of the present invention includes a sealed container; and a wiring board which is housed in the sealed container and on which a functional circuit performing a predetermined function while the capsule-type medical apparatus is inserted into a subject is mounted. The wiring board includes a plurality of rigid wiring board sections on which parts constituting the functional circuit are mounted, and a flexible wiring board section that connects the plurality of the rigid wiring board sections so that the adjacent rigid wiring board sections oppose to each other. Parts with a protruding height that exceeds a predetermined threshold are mounted on the rigid wiring board sections that oppose to each other at such positions that the parts do not oppose to each other.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

An exemplary embodiment of an capsule endoscope, which is an capsule-type medical apparatus, according to the present invention is explained in detail below with reference to the accompanying drawings.

Figure 1:
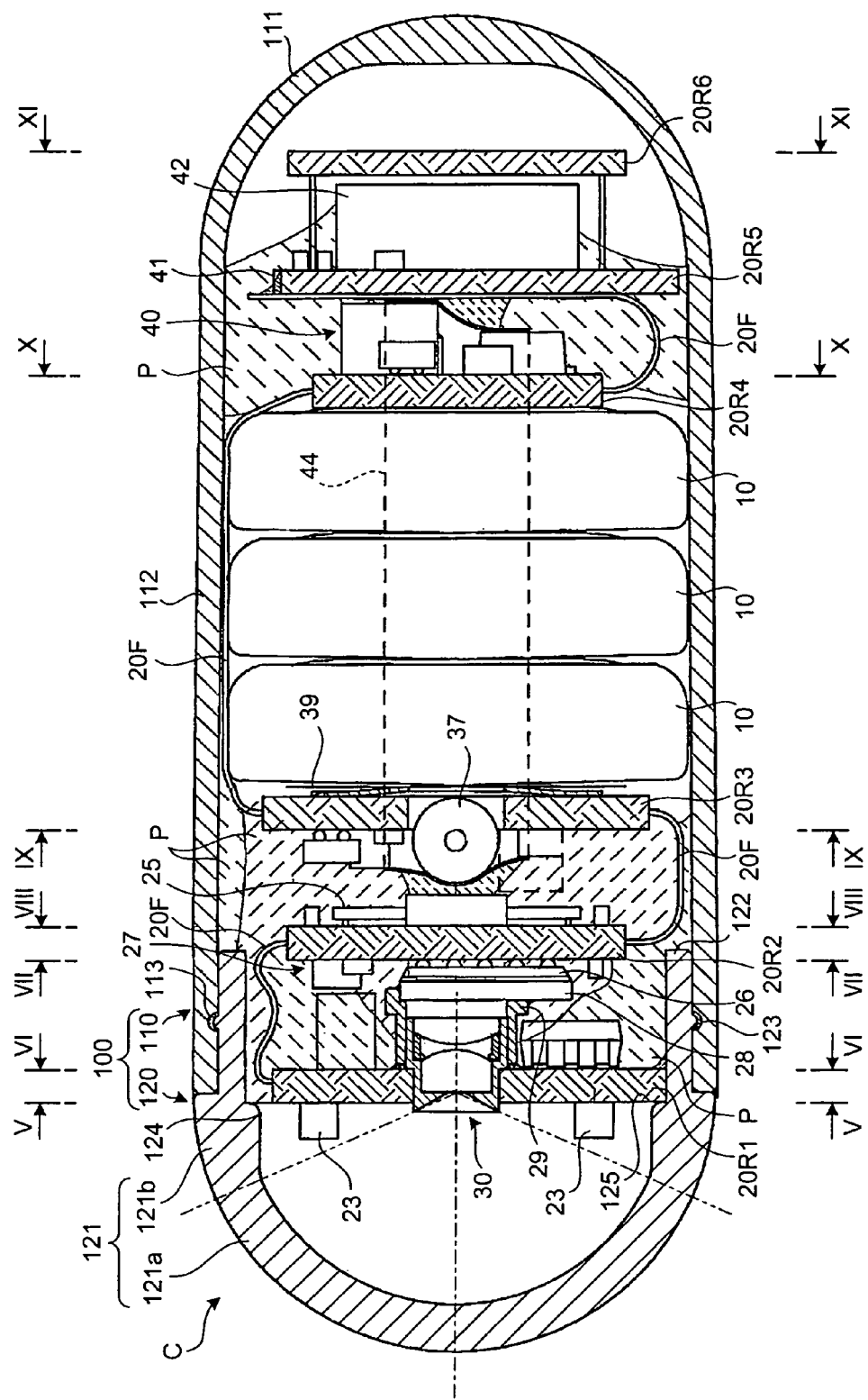
FIG. 1 is a sectional side view of an capsule endoscope, which is an capsule-type medical apparatus, according to an embodiment of the present invention.

FIG. 1 is a sectional side view showing the capsule endoscope according to the embodiment of the present invention. An capsule endoscope C shown here has a size capable of being inserted into a subject body from a mouth of a subject such as a human being, an animal, and the like. The capsule endoscope C acquires image data, which is internal information of alimentary canal such as stomach, small intestine, and large intestine, until the capsule endoscope C is discharged outside from the subject body after the capsule endoscope C is inserted. The capsule endoscope C is provided with internal power supplies 10, a wiring board 20 on which a functional circuit performing a predetermined function is mounted, and a capsule-shaped sealed container 100 that houses the internal power supplies 10 and the wiring board section 20.

The internal power supply 10 accumulates drive electric power that is supplied to the functional circuit. In the present embodiment, three general-purpose silver oxide button cells (hereinafter also referred to as button cell 10) are used as the internal power supplies 10. It is not necessary to use the silver oxide cell as the internal power supply 10, and a battery such as a rechargeable battery and a power generating battery can be used. Further, it is not necessary to have three button cells 10, and the number of cells can be determined in accordance with an operation time of the functional circuit.

The wiring board section 20 is a composite board section provided with a plurality of rigid wiring board sections 20R and a flexible wiring board section 20F connecting the plurality of the rigid wiring board sections 20R in series (hereinafter the wiring board section 20 will be referred to as rigid and flexible wiring board section 20 as appropriate). The rigid wiring board sections 20R made from a comparatively rigid material such as glass epoxy resin, and the rigid wiring board section 20R is a section on which various functional parts and electronic parts constituting the functional circuit are mainly mounted. The flexible wiring board section 20F is made from a comparatively flexible film-like material such as polyimide and polyester resin, and the flexible wiring board section 20F is a section that mainly functions as a cable for electrically connecting the plural rigid wiring board sections 20R to each other.

The functional circuit configured on the wiring board section 20 has a plurality of predetermined functional sections necessary for acquiring the image data. For example, the functional sections have an illumination function that illuminates a predetermined region with an illuminating light, an imaging function that converts a reflective light due to the illumination with the illuminating light into an image signal, a switch function that turns ON/OFF the supplied electric power from the internal power supply 10, a voltage-conversion function that adjusts an internal power supply voltage to a predetermined constant voltage, a transmission processing function that performs modulation and amplification with respect to the acquired image signal, an antenna function that outputs the modulated and amplified image signal to outside as a radio signal, a control function that controls the whole functions.

In the present embodiment, the plural functional sections are divided into plural pieces of the rigid wiring board section 20R. Specifically, the rigid wiring board section 20R of the wiring board section 20 includes an illumination board section 20R1 for implementing the illumination function, an imaging board section 20R2 for implementing the imaging function and the control function, a switch board section 20R3 for implementing the switch function, a power supply board section 20R4 for implementing the voltage conversion function, a transmission board section 20R5 for implementing the transmission processing function, and an antenna board section 20R6 for implementing the antenna function.

The illumination board section 20R1 is disk-shaped as shown in FIGS. 1 to 6, and the illumination board section 20R1 has an attachment hole 21 at a center thereof as well as has a straight-line portion 22R1 at one portion of a periphery face thereof. The attachment hole 21 is a section to which a lens unit 30 described later is mounted, and the attachment hole 21 has a circular shape with a small diameter. The straight-line portion 22R1 is configured by linearly removing penumbra of the illumination board section 20R1, and the straight-line portion 22R1 is provided in a direction orthogonal to an extending direction of the flexible wiring board section 20F.

Figure 4:
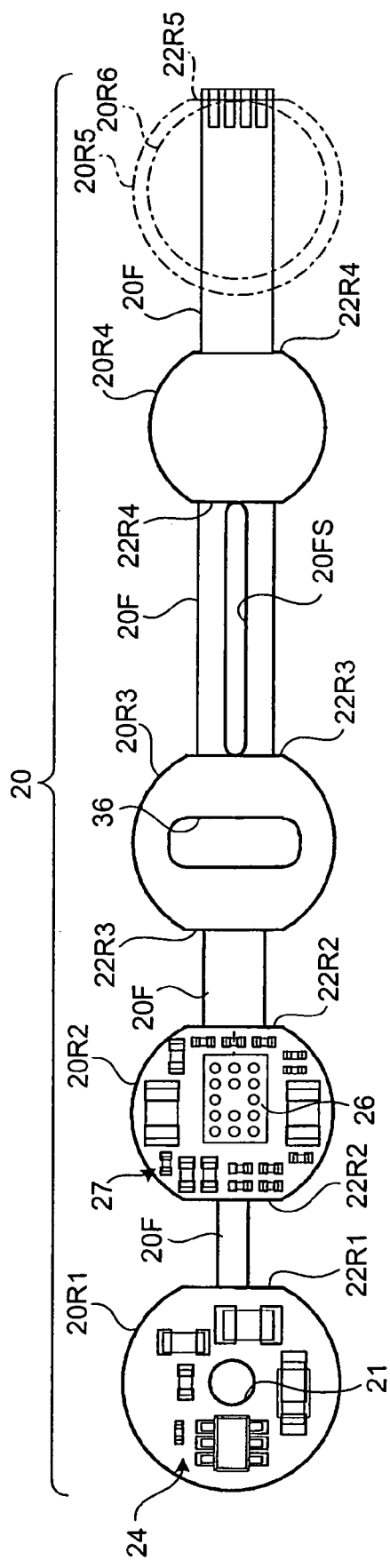
FIG. 4 is a bottom plan view of FIG. 2.

In order to implement the illumination function, an light-emitting device 23 such as a white diode is mounted on one of mounting faces of the illumination board section 20R1, and the electronic part for configuring a drive circuit 24 of the light-emitting device 23 is mounted on the other mounting face of the illumination board section 20R1. Four light-emitting devices 23 are mounted on the illumination board section 20R1 so that distances from the attachment hole 21 and each of the light-emitting devices 23 are equal to others, as well as the light-emitting devices 23 are equally spaced around the attachment hole 21, as shown in FIG. 4. The light-emitting device 23 is not limited to the white diode, and it is possible to use a diode having other color or to use an EL (electroluminescence) device. Further, number of the light-emitting device 23 is not limited to four, and the number can be three or less, or five or more as long as the illumination function is sufficiently implemented.

A first large electronic part 24a for driving the light-emitting device 23, a second large electronic part 24b for supplying steady voltage to the light-emitting device 23, and a small electronic part 24c such as a small capacitor, represent the electronic parts constituting the drive circuit 24 of the light-emitting device 23. The small electronic part 24c such as the small capacitor has sufficiently small protruding height from the mounting face, and the height is much less than a predetermined threshold such as ½ of a space to be obtained between the imaging board section 20R2 and the illumination board section 20R1. On the other hand, the first large electronic part 24a for driving the light-emitting device 23 and the second large electronic part 24b for supplying the steady voltage to the light-emitting device 23 have comparatively large protruding height from the mounting face so that the height exceeds the threshold described above.

The imaging board section 20R2 is disk-shaped and has a diameter the same as or slightly smaller than the diameter of the illumination board section 20R1 as shown in FIGS. 1 to 4, 7, and 8, and the imaging board section 20R2 has two straight-line portions 22R2 at a periphery face thereof. The straight-line portion 22R2 is formed by linearly removing penumbra of the imaging board section 20R2, and the straight-line portions 22R2 are provided in parallel to each other as well as provided orthogonally with respect to the extending direction of the flexible wiring board section 20F.

A processor element for implementing the control function, such as a DSP (Digital Signal Processor) (hereinafter simply referred to as DSP 25), and an electronic part are mounted on one of mounting faces of the imaging board section 20R2. Further, an imaging element for realizing the imaging function, such as a CCD (Charge Coupled Device) and a CMOS (Complementary Metal Oxide Semiconductor) (hereinafter simply referred to as CCD 26), and an electronic part constituting the drive circuit 27 of the CCD 26 are mounted on the other mounting face of the imaging board section 20R2. The DSP 25 mainly controls driving of the capsule endoscope C, signal process of the CCD 26, and driving of the illumination board section 20R1.

Figure 12:
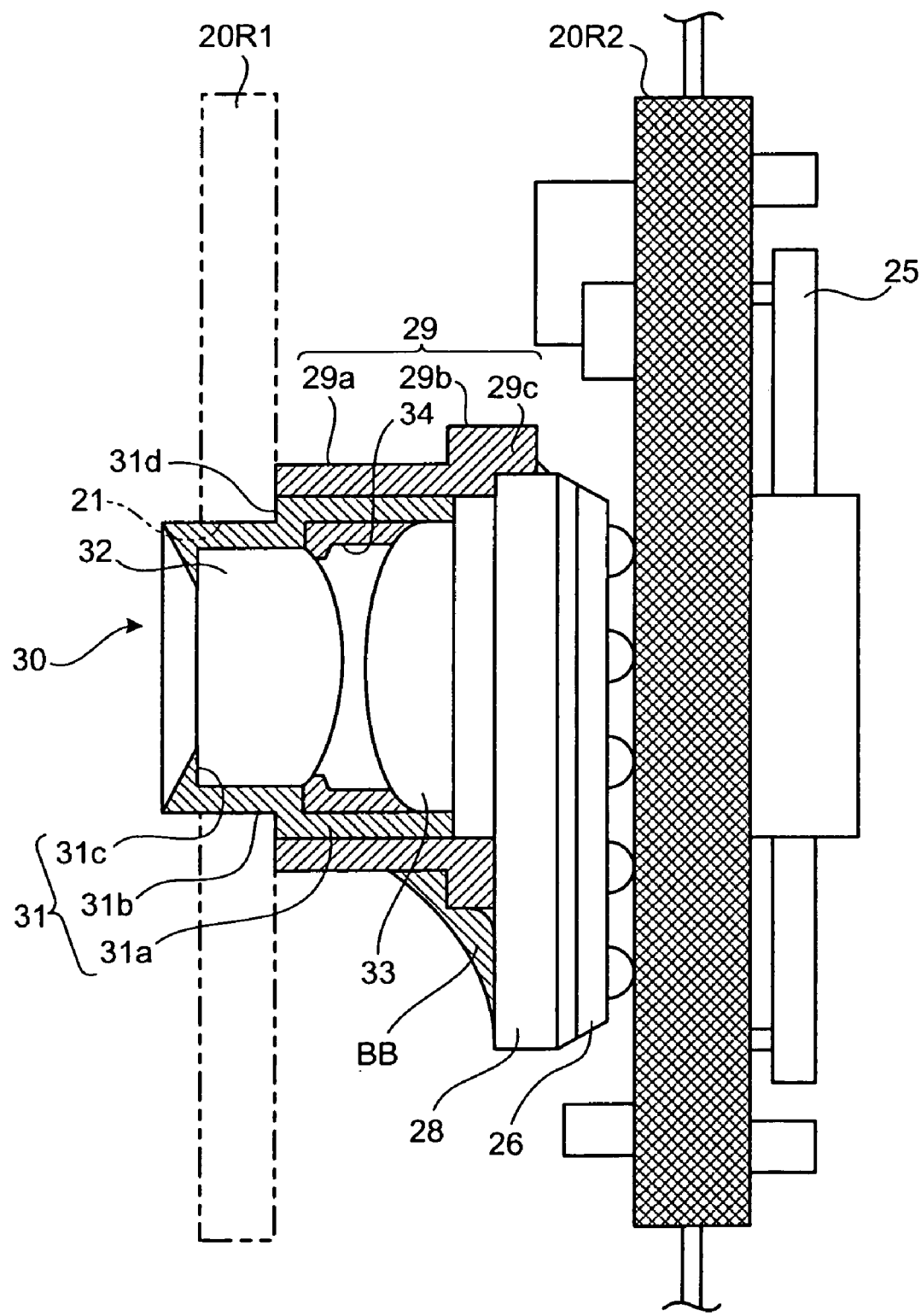
FIG. 12 is an enlarged sectional view showing a relevant part of the internal member used for the capsule endoscope shown in FIG. 1.
Figure 13:
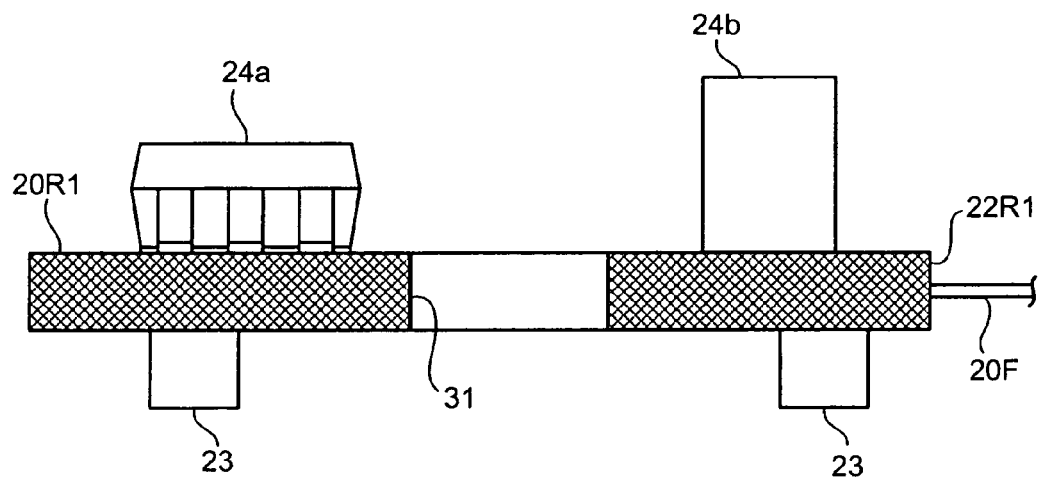
FIG. 13 is a sectional side view of an imaging board section.

The CCD 26 has a rectangular outline, and is provided as a ball grid array package so that a direction of pixel array thereof is along the straight-line portion 22R2 of the imaging board section 20R2. A holding frame 29 is provided on a pixel face of the CCD 26 through a cover glass 28, and a lens unit 30 is mounted inside the holding frame 29 as shown in FIGS. 1 and 12.

The cover glass 28 has a rectangular flat plate shape with substantially the same size as an upper face of the CCD 26, and the cover glass 28 covers substantially entire upper face of the CCD 26. The holding frame 29 has a cylindrical-portion 29a that has cylindrical shape with a diameter larger than the pixel face of the CCD 26, and has a base 29b that is formed integrally with the cylindrical portion 29a at a proximal end of the cylindrical portion 29a. The holding frame 29 is attached to the cover glass 28 through the base portion 29b so that a central axis of a field of view at the CCD 26 matches a center of axis of the cylindrical portion 29a. Further, in the base portion 29b of the holding frame 29, a positioning portion 29c and a reinforcing portion 29d are projected in level with respect to each other at an end face of the cover glass 28 and at a side face of the cover glass 28. The positioning portion 29c determines a position of the holding frame 29 and the cover glass 28 along one direction while the end face of the cover glass 28 is brought into contact with the positioning portion 29c. Further, the reinforcing portion 29d determines a position of the holding frame 29 and the cover glass 28 along another direction, while the cover glass 28 is brought into contact with the reinforcing portion 29d. A section between the cover glass 28 and the holding frame 29, and an exposed face of the cover glass 28 that are not covered by the holding frame 29 are coated by a black bonding agent BB. Consequently, unnecessary light incidence from the exposed face can be avoided, and a clear image can be projected on the CCD 26.

The lens unit 30 includes a cylindrical lens frame 31 and a pair of large and small lens members 32 and 33. A cylindrical slide portion 31a with a comparatively large diameter that has an exterior diameter fitting into the cylindrical portion 29a of the holding frame 29, a cylindrical attachment portion 31b with a comparatively small diameter that has an exterior diameter fitting into the Attachment hole 21 of the illumination board section 20R1, and a light-shielding portion 31c that is projected inwards from an entire periphery of a distal end of the attachment portion 31b, together form the lens frame 31. Here, the attachment portion 31b is connected to a distal end of the slide portion 31a coaxially. A shoulder portion 31d is configured between the slide portion 31a and the attachment portion 31b, at an exterior periphery face of the lens frame 31. The light-shielding portion 31c corresponds to an entrance pupil that determines an observed region of the image data with respect to the lens unit 30. An exterior end face of the light-shielding portion 31c is taperedly sunk towards a central axis of the lens unit 30.

A collar member 34 is lying between the pair of the lens members 32 and 33, and the lens members 32 and 33 are mounted inside the lens frame 31 with optical axes of the lens members 32 and 33 matched to each other. The lens member 32 with a small diameter has a flat plane at a front side thereof and a convex plane at a backside thereof, and the lens member 32 has a comparatively large index of refraction of light. The lens member 32 is mounted at a front side of the lens frame 31. The lens member 33 with a large diameter has a convex plane at a front side thereof, which is a side opposing to the lens member 32 with the small diameter, and has a flat plane at a backside thereof. The lens member 33 has a comparatively small index of refraction of light, and the lens frame 33 is mounted at a backside of the lens frame 31.

The lens unit 30 is slidably disposed in the cylindrical portion 29a of the holding frame 29 through the slide portion 31a while arranging the light-shielding portion 31c outwards, and a focus can be adjusted by appropriately shifting the lens unit 30 along the optical axis direction with respect to the pixel face of the CCD 26. The holding frame 29 and the lens unit 30 are preferably fastened to each other after the focus is adjusted.

Figure 7:
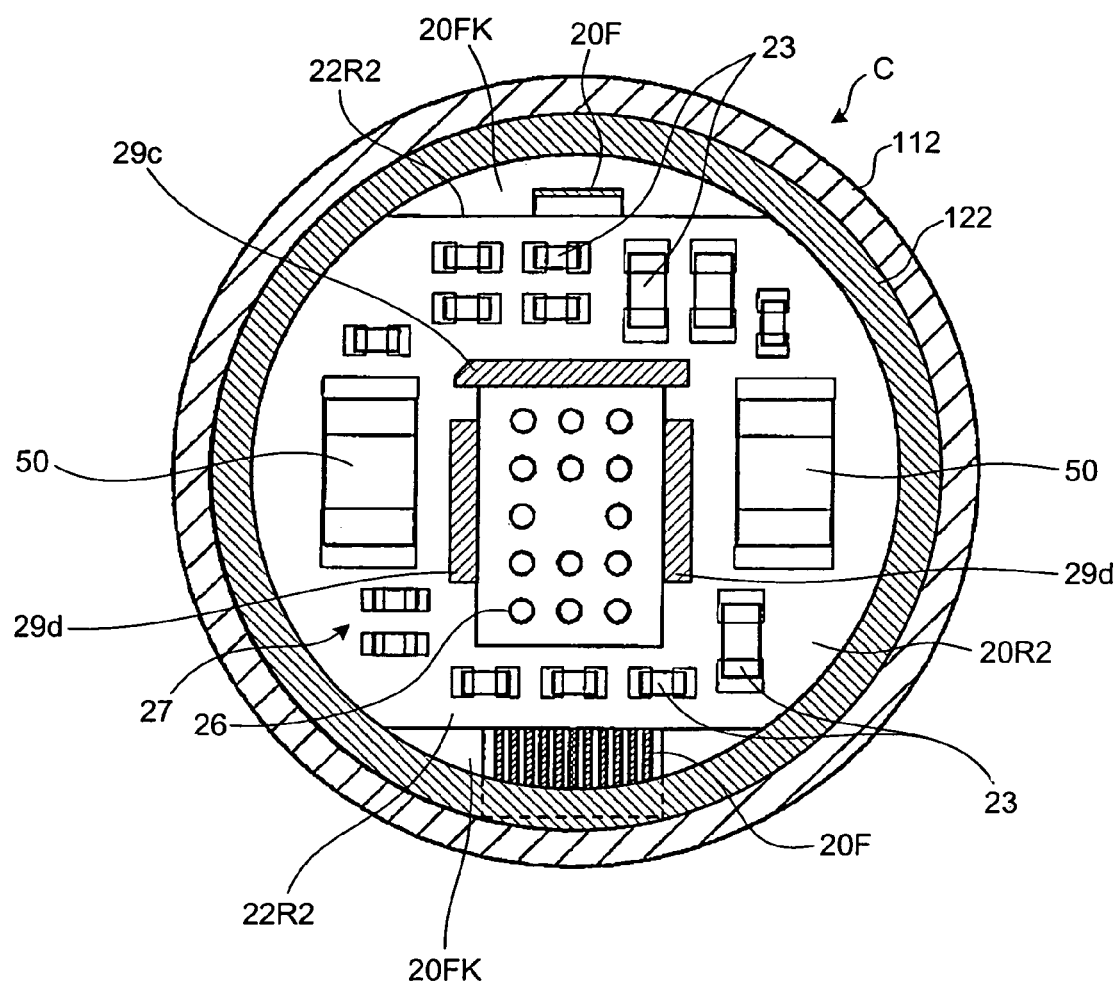
FIG. 7 is a VII-VII sectional view of FIG. 1.
Figure 14:
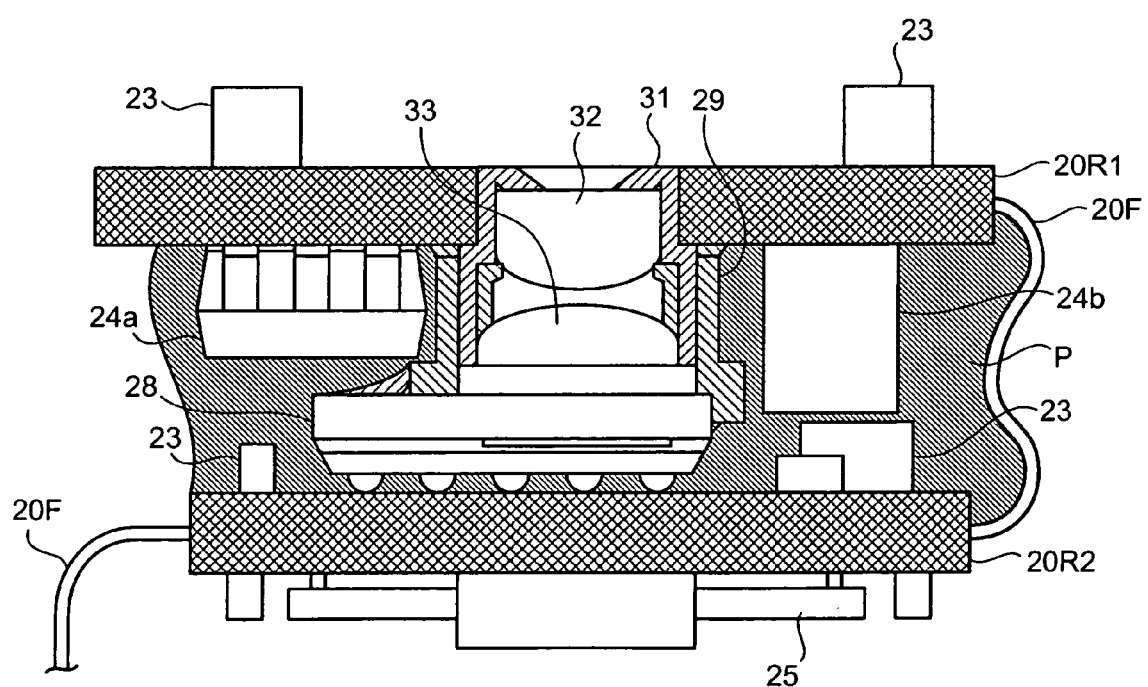
FIG. 14 is a sectional side view showing lamination layers of the imaging board section and an illumination board section.
Figure 15:
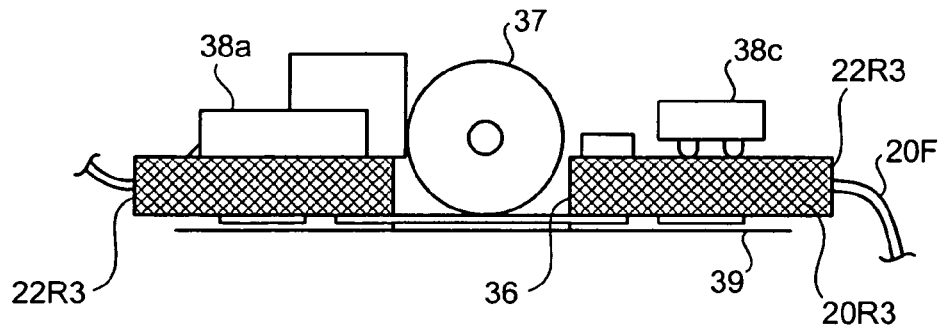
FIG. 15 is a sectional side view showing a switch board section.
Figure 16:
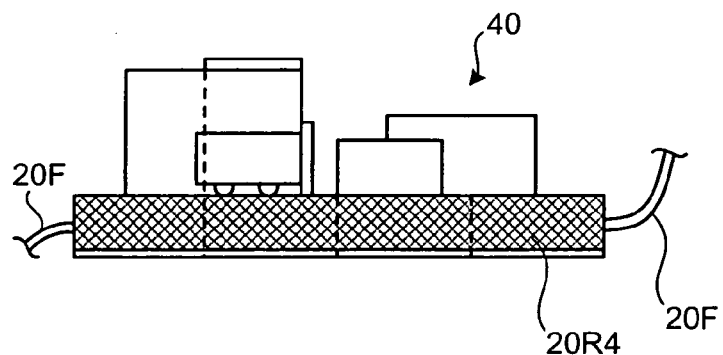
FIG. 16 is a sectional side view of a power supply board section.
Figure 17:
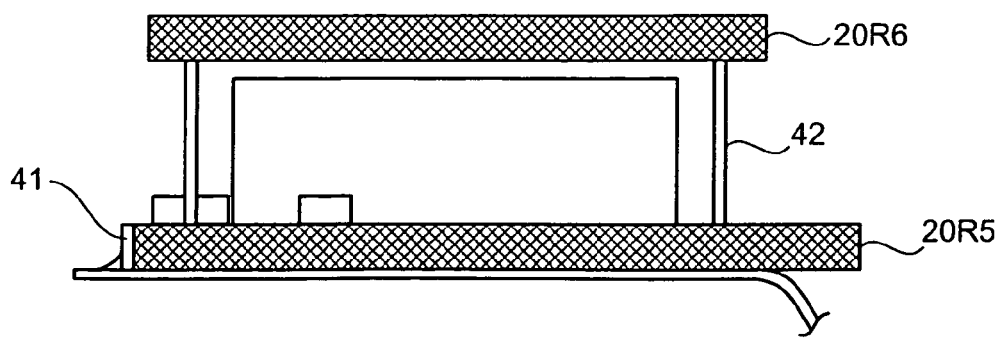
FIG. 17 is a sectional side view showing an RF unit.

A large electronic part 50 such as a capacitor for power supply voltage circuit to drive the CCD 26 and a small electronic part 51 such as a capacitor and a resistor necessary for driving the CCD 26 are arranged at a front face of the imaging board section 20R2 as shown in FIGS. 7 and 14. A protruding height of the large electronic part 50 from a mounting face of the imaging board section 20R2 is comparatively large so that the protruding height exceeds the threshold described above, whereas a protruding height of the small electronic part 51 from the mounting face of the imaging board section 20R2 is much less than the threshold. Here, any specific limitation is not provided for a mounting position of the small electronic part 51; however, there is a limitation for a mounting position of the large electronic part 50. That is to say, the large electronic part 50 is provided only at a position opposing to the small electronic part 24c mounted on the other mounting face of the illumination board section 20R1, or at a position apart from the electronic parts 24a, 24b, and 24c mounted on the other mounting face of the illumination board section 20R1, while folding the flexible wiring board section 20F to oppose the imaging board section 20R2 and the illumination board section 20R1 to each other.

Figure 8:
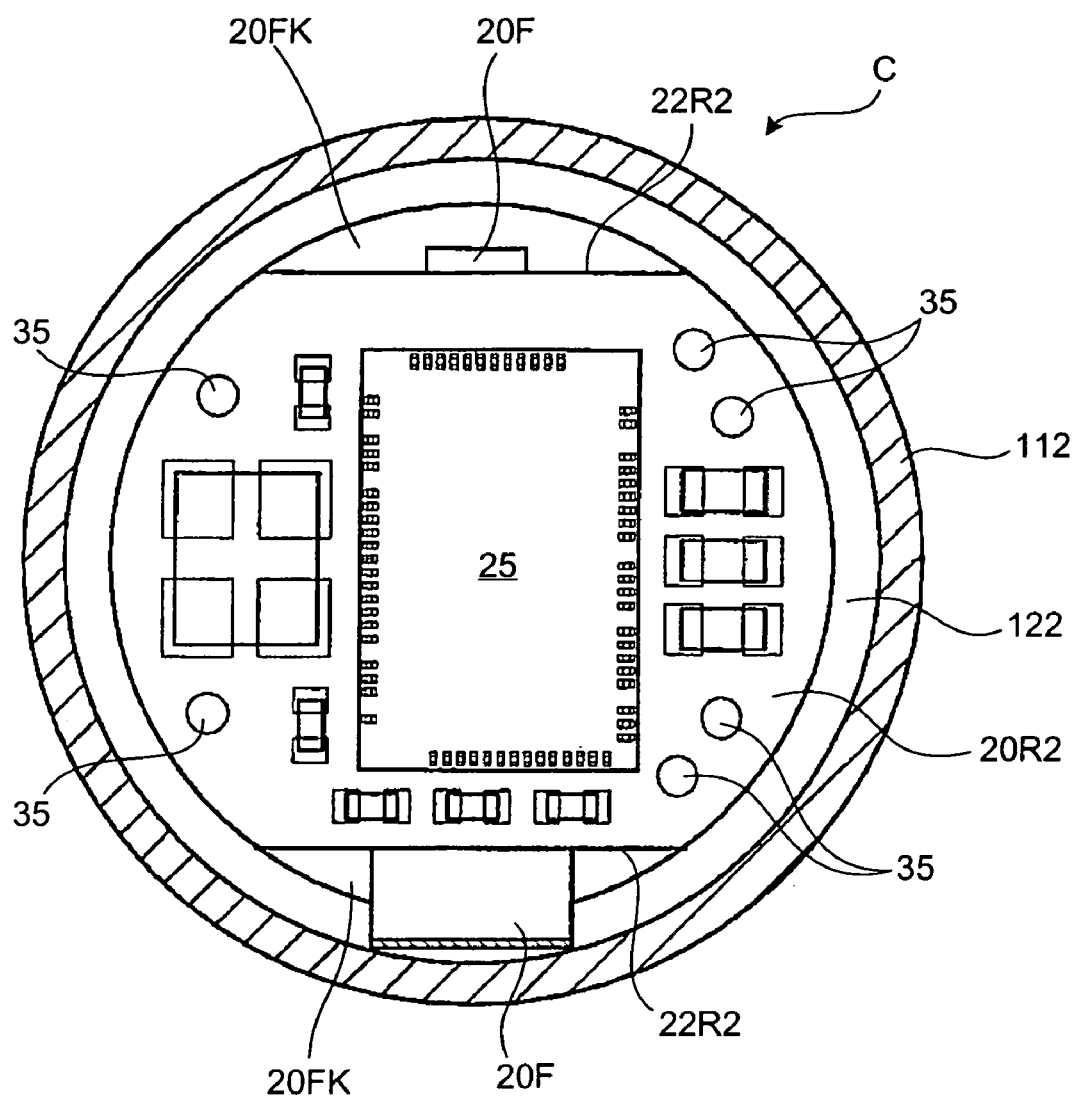
FIG. 8 is a VIII-VIII sectional view of FIG. 1.
Figure 9:
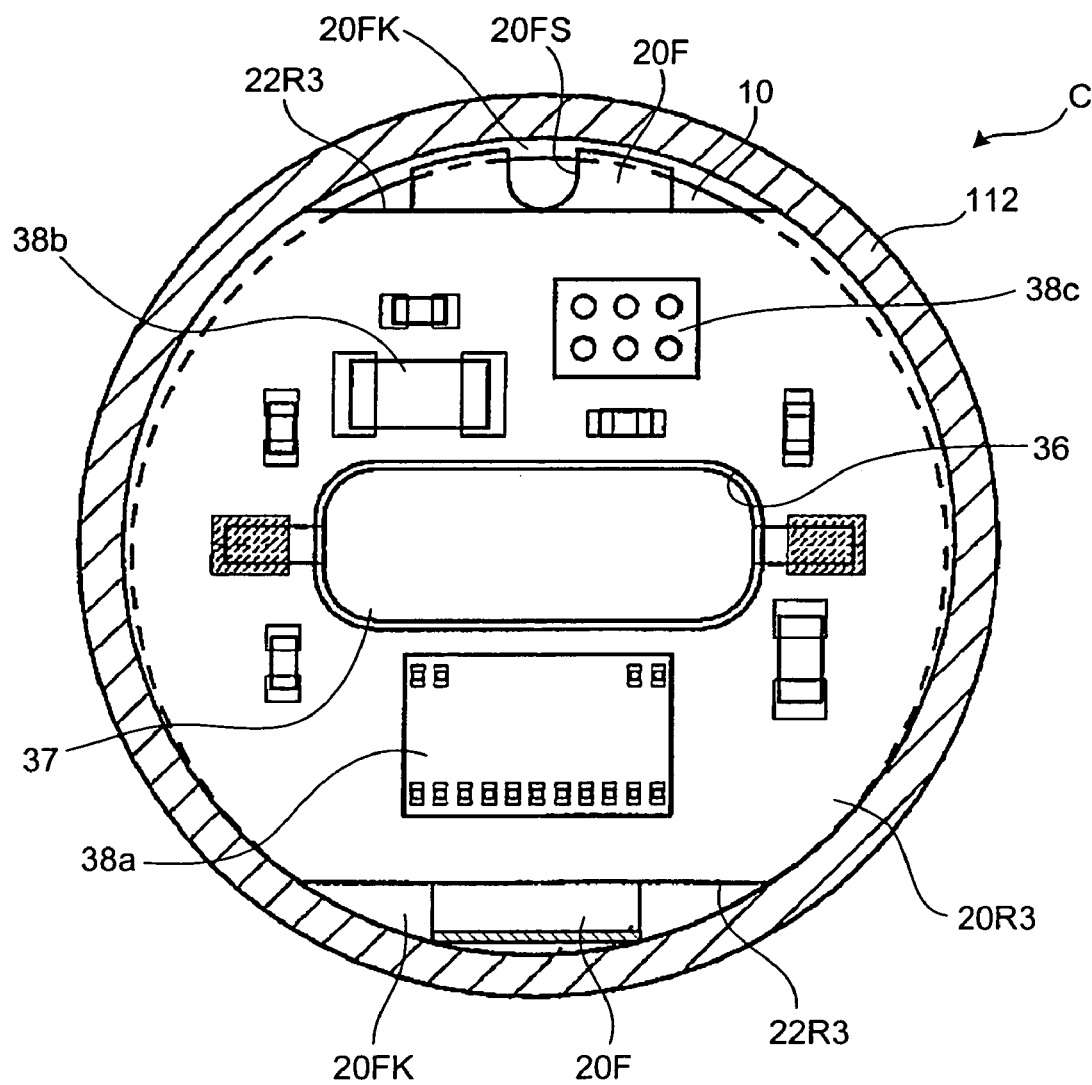
FIG. 9 is a IX-IX sectional view of FIG. 1.

Further, plural pad portions 35, which are external terminals, are provided at sections outside of a mounting region of the electronic part and the like on one mounting face of the imaging board section 20R2 as shown in FIG. 8. The pad portions 35 are conductor sections roundly exposed from the mounting face of the imaging board section 20R2. The pad portion 35 is provided with a section that functions as an exterior power supply terminal for supplying electric power directly to the functional circuit from an exterior power supply not shown, and provided with a section that functions as an exterior input terminal for supplying default setting value of the functional circuit to a memory 38a described below.

The switch board section 20R3 is disk-shaped and has a same or smaller diameter compared to the diameter of the imaging board section 20R2 as shown in FIGS. 1 to 4, 9, and 15. The switch board section 20R3 has two straight-line portions 22R3 at a periphery face as similar to the imaging board section 20R2, as well as the switch board section 20R3 has an relief hole 36 at a central section thereof. The straight-line portion 22R3 is configured by linearly removing penumbra of the switch board section 20R3, and the straight-line portions 22R3 are provided so that the straight-line portions 22R3 are in parallel to each other as well as the straight-line portions 22R3 are orthogonal to the extending direction of the flexible wiring board section 20F. The relief hole 36 is for housing a part of a reed switch 37 described below, and the relief hole 36 is formed in a long hole shape extending along the straight-line portion 22R3.

The reed switch 37 for implementing the switch function is mounted on one of the mounting faces of the switch board section 20R3 while a part of the reed switch 37 being housed in the relief hole 36, as well as the electronic part such as the memory 38a, a transducer 38b, and a mixer device 38c are mounted around the relief hole 36 on one of the mounting faces.

The reed switch 37 responds to a magnetic field and turns ON/OFF the electric power supplied from the internal power supply 10. In the present embodiment, the electric power supply from the internal power supply 10 is turned OFF when the magnetic field is caused, for example, by placing a permanent magnet close to the reed switch 37, and the electric power supply from the internal power supply 10 is continuously turned ON when the magnetic field does not exist.

The memory 38a is a volatile memory unit that stores data such as a default setting value of the DSP 25 necessary for driving the functional circuit. Data for compensating white balance coefficient of the CCD 26 and fluctuation of the CCD 26, and pixel deficiency address data of the CCD 26 represent, for example, the default setting value of the DSP 25. The transducer 38b provides a basic clock to the DSP 25. The mixer device 38c is mounted by flip chip bonding, and the mixer device 38c has a function of mixing an image signal and a clock signal output from the DSP 25. A disk-spring-like positive electrode contact member 39, which is a contact point with respect to a positive electrode of the button cell 10, is provided on the other mounting face of the switch board section 20R3 as shown in FIG. 1.

The power supply board section 20R4 is disk-shaped, and has a smaller diameter than the diameter of the switch board section 20R3 as well as a diameter of a negative electrode of the button cell 10, as shown in FIGS. 1 to 4, 10, and 16. Further, the power supply board section 20R4 has two straight-line portions 22R4 at periphery face as similar to the switch board section 20R3. The straight-line portion 22R4 is formed by linearly removing penumbra of the power supply board section 20R4, and the straight-line portions 22R4 are in parallel to each other as well as orthogonal to the extending direction of the flexible wiring board section 20F.

Plural electronic parts such as DC-DC converter 40 for implementing the voltage conversion function are provided on one of mounting faces of the power supply board section 20R4. The DC-DC converter 40 controls a voltage acquired from the button cell 10 in order to acquire steady voltage necessary for the capsule endoscope C. A negative electrode contact member, which is a contact point with respect to a negative electrode of the button cell 10, is provided on the other mounting face of the power supply board section 20R4, although not clearly shown in the drawings.

The transmission board section 20R5 is disk-shaped, has a same or slightly smaller diameter compared to the diameter of the switch board section 20R3, and has a straight-line portion 22R5 at one part of a periphery face as similar to the illumination board section 20R1 as shown in FIGS. 1, 2, 4, and 11. The straight-line portion 22R5 is formed by linearly removing penumbra of the transmission board section 20R5, and the straight-line portion 22R5 has a plurality of through-hole lands 41.

An end of the flexible wiring board section 20F is connected to one of mounting faces of the transmission board section 20R5 through the through-hole land 41 as well as a plurality of the electronic parts such as an RF (Radio Frequency) unit 42 for implementing the transmission processing function are mounted on the other mounting face of the transmission board section 20R5.

Figure 11:
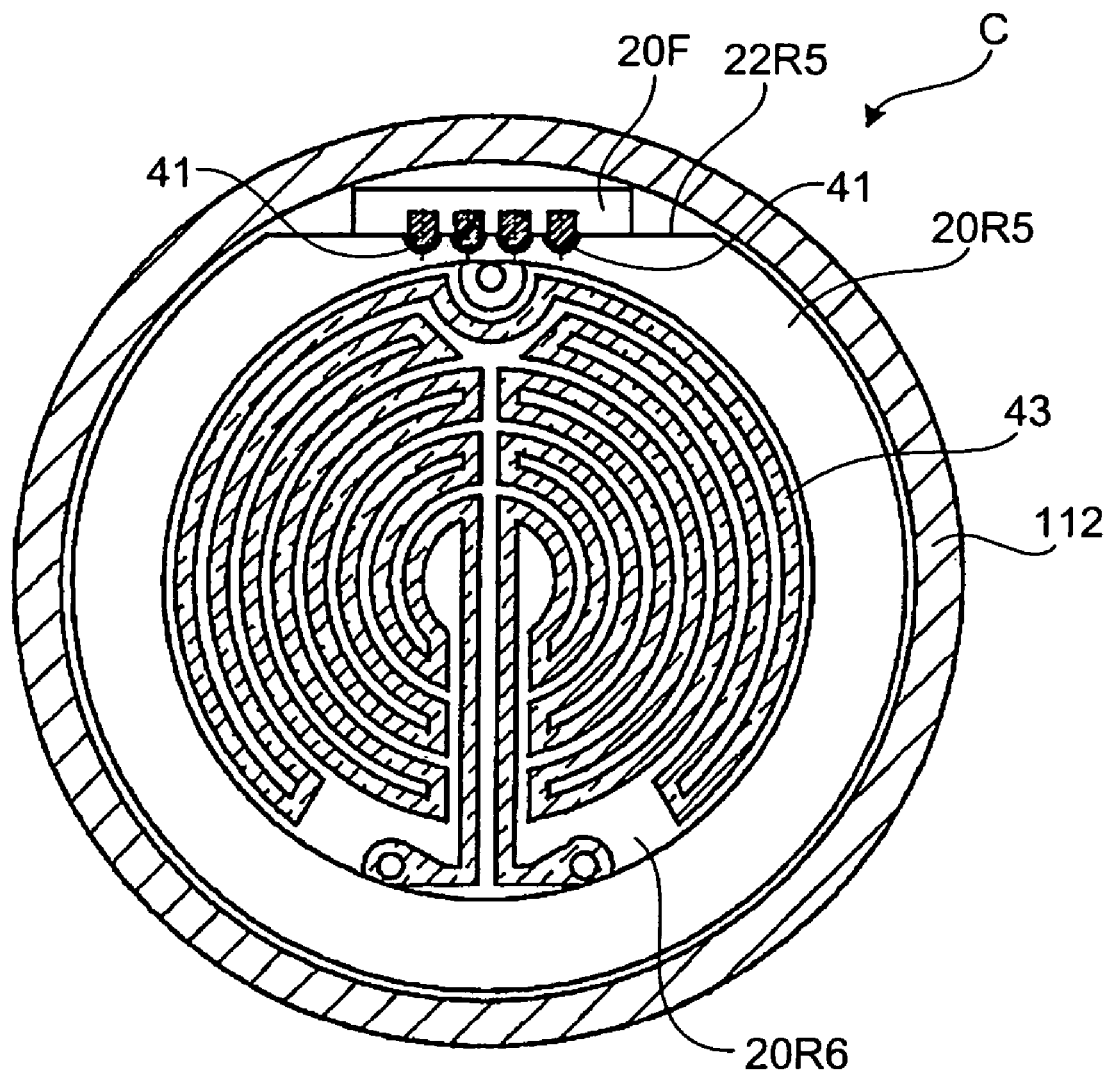
FIG. 11 is a XI-XI sectional view of FIG. 1.

The antenna board section 20R6 is disk-shaped and has a diameter smaller than the diameter of the transmission board section 20R5, and the antenna board section 20R6 is attached to the other mounting face side of the transmission board section 20R5 so that the antenna board section 20R6 and the transmission board section 20R5 are in parallel to each other as shown in FIGS. 1 and 11. An antenna 43 is formed on the antenna board section 20R6 by arranging a conducting wire substantial spirally. Both ends of the conducting wire constituting the antenna 43 are each electrically connected to a circuit section of the transmission board section 20R5, although not shown in the drawings.

Figure 2:
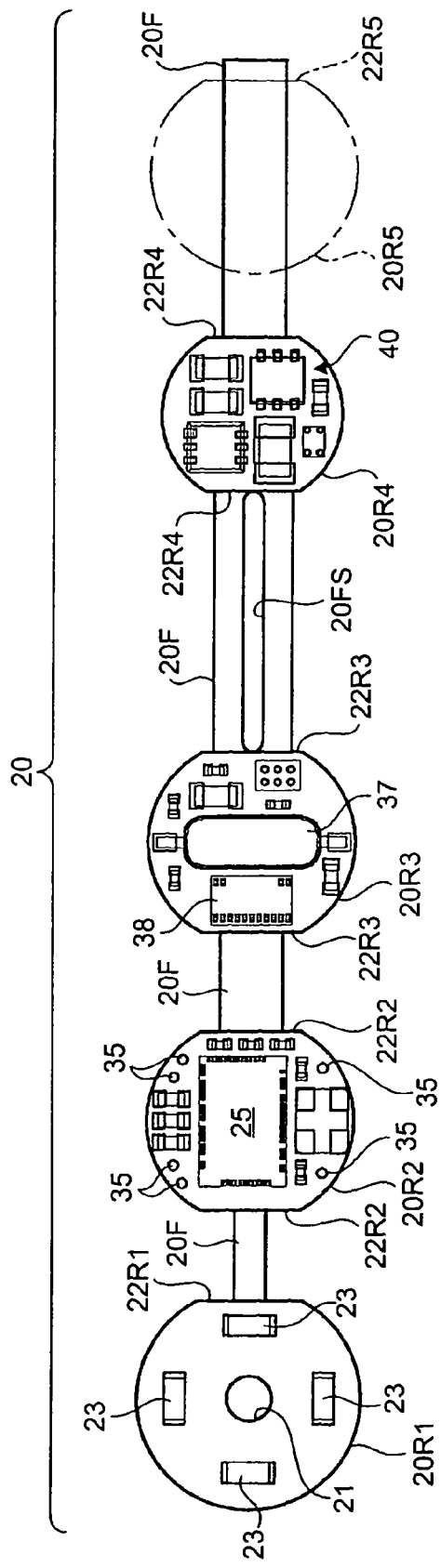
FIG. 2 is a development plan view of a wiring board section that is an internal member of the capsule endoscope shown in FIG. 1.
Figure 3:
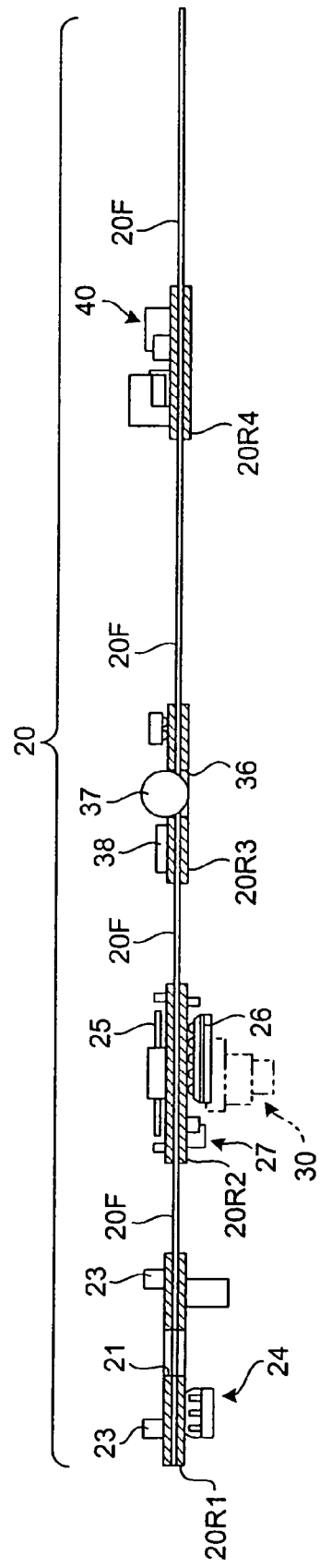
FIG. 3 is a sectional side view of FIG. 2.

The illumination board section 20R1, the imaging board section 20R2, the switch board section 20R3, the power supply board section 20R4, and the transmission board section 20R5 of the rigid wiring board section 20R are preliminary connected to each other in series with the order written above by the flexible wiring board section 20F, as shown in FIGS. 2 to 4. From the illumination board section 20R1 to the power supply board sections 20R4 of the rigid wiring board sections 20R are formed together in a flat plate shape with the flexible wiring board section 20F, and the electronic parts are mounted on each of the rigid wiring board sections 20R from the illumination board section 20R1 to the power supply board section 20R4. Then, the transmission board section 20R5, which is formed together with the antenna board section 20R6, is connected to an end of the flexible wiring board section 20F, whereby the straight rigid and flexible wiring board 20 is configured.

Here, it is possible to easily mount the electronic parts on the rigid wiring board section 20R from the illumination board section 20R1 to the power supply board section 20R4, which configures the flat plate with the flexible wiring board section 20F, by a general mounting technique. Further, it is not necessary to electrically connect the rigid wiring board section 20R and the flexible wiring board section 20F that are formed together because the rigid wiring board section 20R and the flexible wiring board section 20F are already electrically connected to each other at a production process thereof. Consequently, it is possible to shorten a production process as well as to simplify an assembly operation.

The flexible wiring board section 20F arranged between the rigid wiring board sections 20R are configured to have different width and length according to needs. The flexible wiring board section 20F arranged between the switch board section 20R3 and the power supply board section 20R4 is configured to have comparatively wide width, and the flexible wiring board section 20F is divided into two by a slit 20FS formed along an elongated direction of the flexible wiring board section 20F.

With respect to the straight rigid and flexible wiring board 20, operation of the functional circuit is tested first. Then, the flexible wiring board section 20F is appropriately folded so that the adjacent rigid wiring board sections 20R oppose to each other as shown in FIG. 1. Further, the button cell 10 is held between the positive electrode contact member 39 of the switch board section 20R3 and the negative electrode contact member (not shown) of the power supply board section 20R4 while matching the negative and positive electrode of the button cell 10 therebetween. Consequently, the rigid and flexible wiring board 20 is blocked in cylindrical shape as an internal member capable of being housed in the sealed container 100.

The operation test is for testing whether or not the functional circuit operates normally when the electric power is supplied to the functional circuit. For the rigid and flexible wiring board 20 having the configuration described above, it is possible to test the operation of the functional circuit while having the rigid and flexible wiring board 20 straight as shown in FIGS. 2 to 4. That is to say, the electrical power can be supplied to the functional circuit by, for example, contacting a spicular electrode of an exterior power supply to the pad portion 35, which functions as the external power supply terminal, for the rigid and flexible wiring board 20 that is provided with the pad portion 35 on the imaging board section 20R2. Therefore, the operation of the functional circuit can be tested and the accurate operation can be ensured even before the button cell 10, which is the internal power supply, is held between the positive electrode contact member 39 and the negative electrode contact member (not shown), such as at a manufacturing line of the rigid and flexible wiring board 20.

Further, an operation time of the functional circuit due to the button cell 10 can be sufficiently maintained even if a comparatively small button cell 10 is used because the external power supply is used to test the operation so that the button cell 10, which is the internal power supply, is not consumed. Furthermore, initializing process such as inputting of the default setting value of the functional circuit to the memory 38a of the switch board section 20R3 through the pad portion 35, which functions as the external input terminal, can be performed together with the electric power supply by the external power supply, if necessary.

In order to bend the flexible wiring board section 20F after the operation test, the attachment portion 31b of the lens unit 30 is fitted into the attachment hole 21 of the illumination board section 20R1 while opposing the other mounting face of the illumination board section 20R1 with respect to the other mounting face of the imaging board section 20R2 as shown in FIG. 1. The lens unit 30 fitted into the attachment hole 21 of the illumination board section 20R1 is positioned and held by the illumination board section 20R1 while the shoulder portion 31d, which is formed between the slide portion 31a and the attachment portion 31b of the lens frame 31, is brought into contact with the other mounting face of the illumination board section 20R so that the optical axes of the lens members 32 and 33, and the central axis of the visual field are each matched to the central axis of the illumination board section 20R1.

In the configuration described above, the CCD 26 and the imaging board section 20R2 can be shifted together with respect to the lens members 32 and 33 by sliding the cylindrical portion 29a of the holding frame 29 with respect to the slide portion 31a of the lens frame 31, so that the focus of the CCD 26 can be adjusted. After the focus of the CCD 26 is adjusted, the illumination board section 20R1 and the imaging board section 20R2 are bonded together by filling and hardening the space therebetween by a resin sealant P such as an insulated bonding agent therebetween.

One of the mounting faces of the imaging board section 20R2 is configured so that the mounting face of the imaging board section 20R2 opposes to one of the mounting faces of the switch board section 20R3. Then, the flexible wiring board section 20F is folded so that the other mounting face of the switch board section 20R3 opposes to the other mounting face of the power supply board section 20R4. Consequently, the button cell 10 is held between the positive electrode contact member 39 and the negative electrode contact member (not shown).

After holding the button cell 10 between the switch board section 20R3 and the power supply board section 20R4, the button cell 10, the switch board section 20R3, and the power supply board section 20R4 are surrounded by a heat-shrinkable tube 44 so that the button cell 10 is compressed and bonded together with the switch board section 20R3 and the power supply board section 20R4, by heating appropriately. Then, each of a space between the imaging board section 20R2 and the switch board section 20R3 and a space between the power supply board section 20R4 and the transmission board section 20R5 are filled with the resin sealant P such as the insulated bonding agent, and the resin sealant P is hardened in order to maintain the space between each of the rigid wiring board sections 20R in a bonded state.

The flexible wiring board section 20F can be easily and accurately folded at a constant position along a boundary line between the rigid wiring board section 20R and the flexible wiring board section 20F, in the rigid and flexible wiring board 20 in which the plural comparatively rigid wiring board sections 20R are connected by the comparatively flexible wiring board section 20F when the internal member of the cylindrical shape is configured as described above. Specifically, each of the flexible wiring board sections 20F can be folded easily and surely at a position close to the rigid wiring board section 20R along each of the straight-line portions 22R since the flexible wiring board section 20F is extended in the orthogonal direction with respect to each of the straight-line portions 22R of the disk-shaped rigid wiring board section 20R, in the present embodiment.

Figure 5:
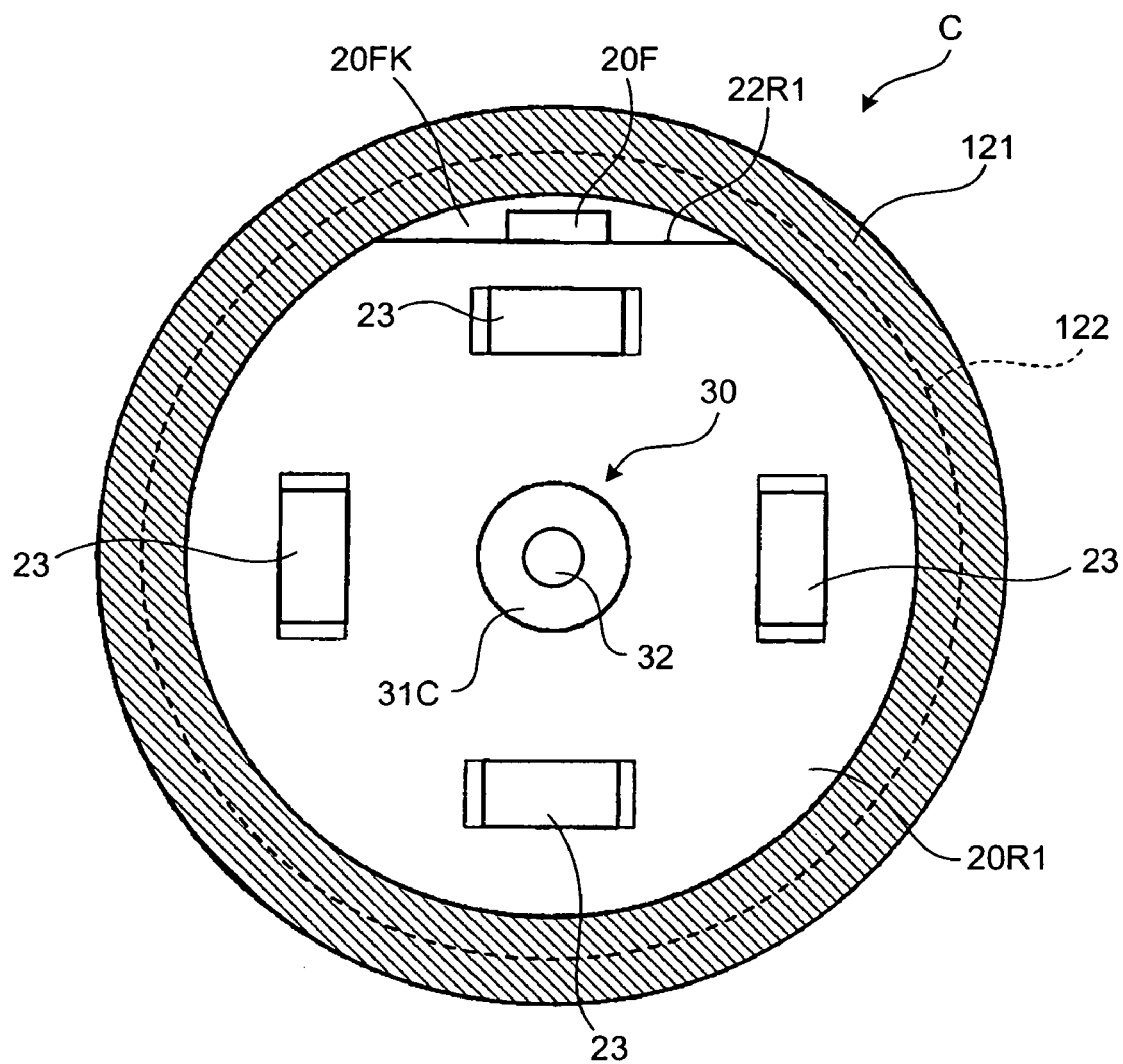
FIG. 5 is a V-V sectional view of FIG. 1.
Figure 6:
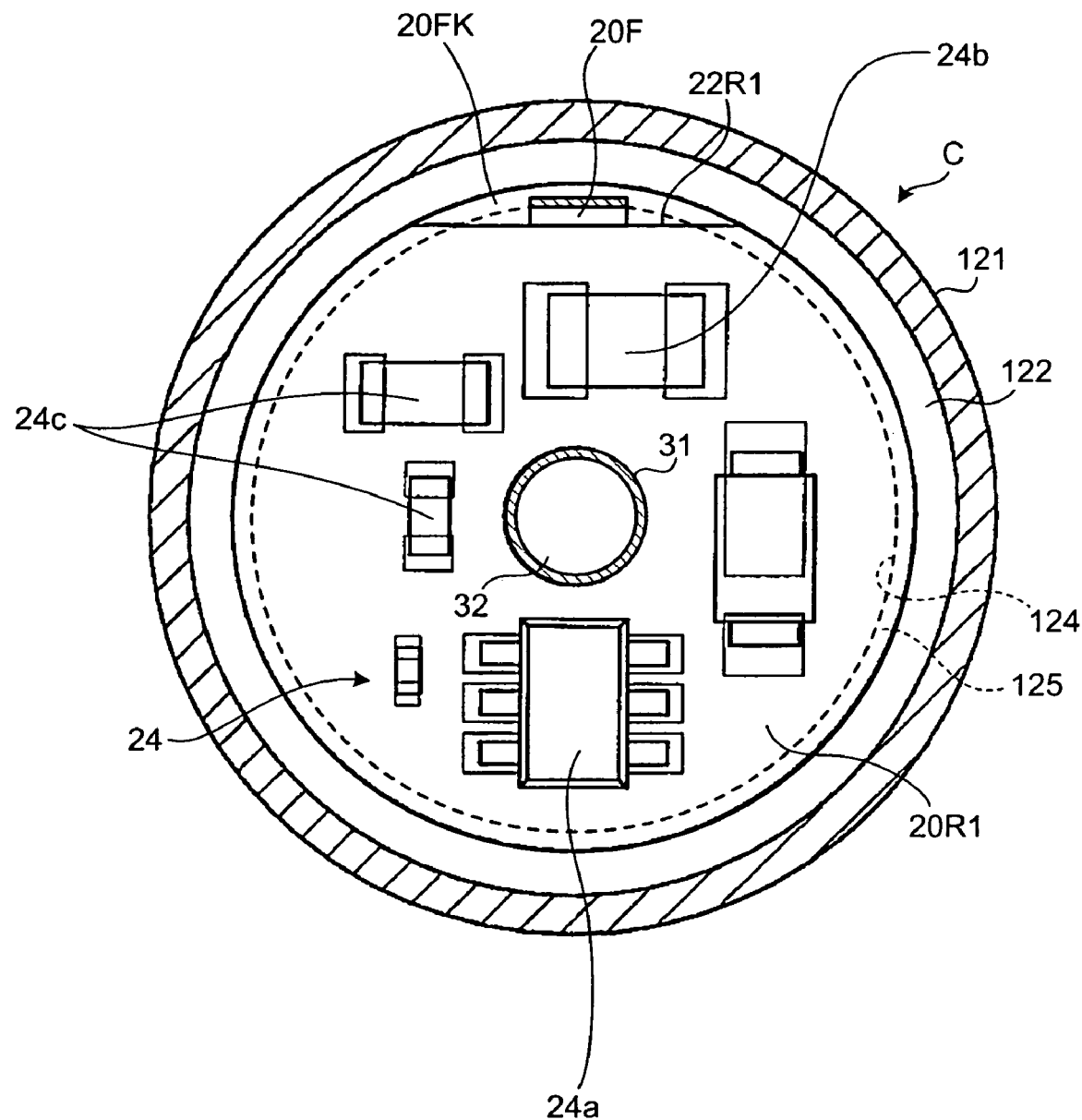
FIG. 6 is a VI-VI sectional view of FIG. 1.
Figure 10:
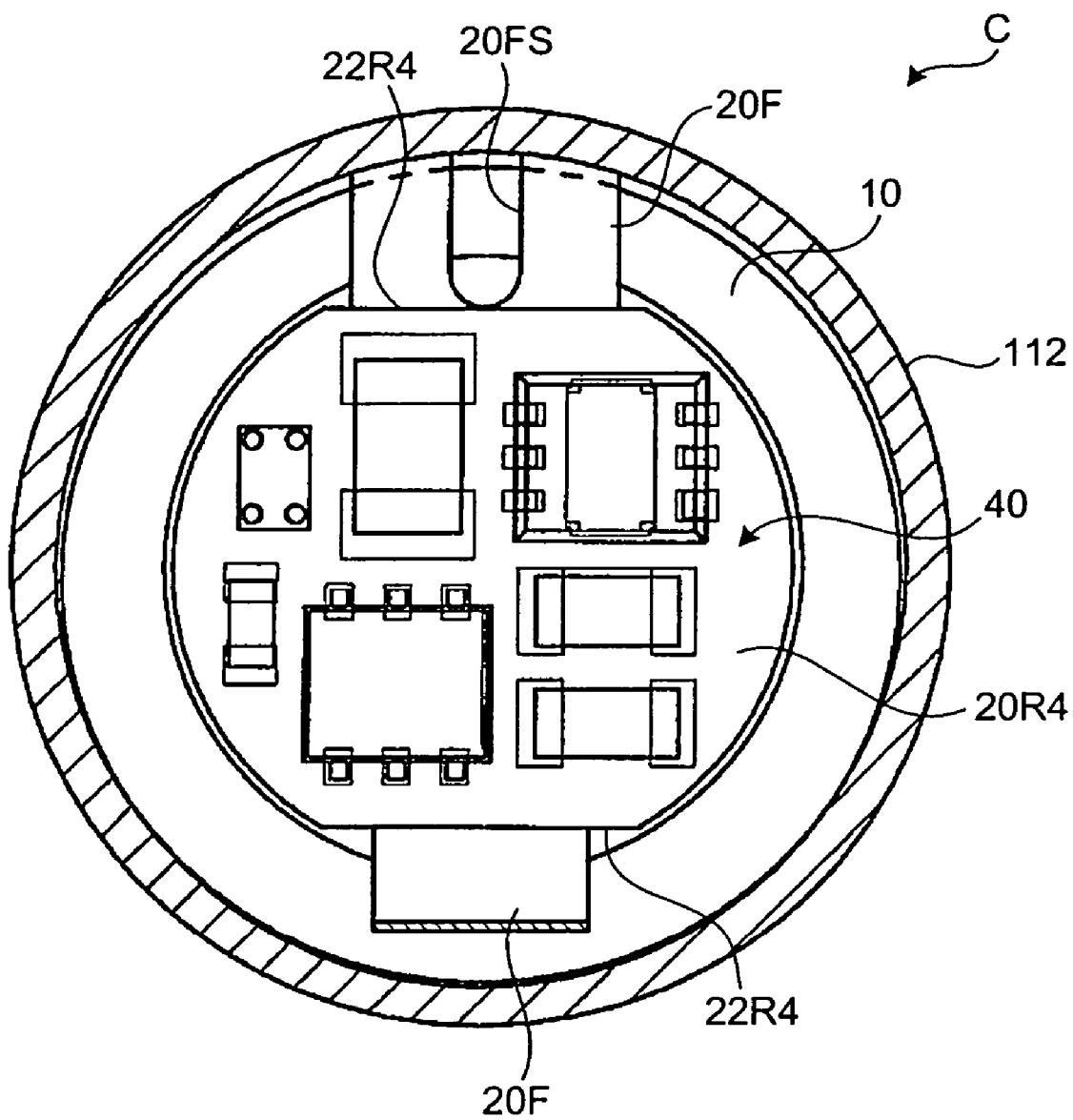
FIG. 10 is a X-X sectional view of FIG. 1.

Further, each of the straight-line portions 22R are formed by removing penumbra of the disk-shaped rigid wiring board section 20R so that the folded flexible wiring board section 20F can be stored in the section corresponding to the removed section, as shown in FIGS. 5 and 6, for example. Furthermore, the flexible wiring board section 20F positioning at outer periphery of the button cell 10 is divided into two by the slit 20FS along the elongated direction of the flexible wiring board section 20F; therefore, the flexible wiring board section 20F is closely arranged at the periphery face of the button cell 10 as shown in FIGS. 10 and 11. As a result, enlargement of the exterior dimension of each of the rigid wiring board sections 20R and the exterior dimension of the button cell 10 due to the flexible wiring board section 20F can be avoided.

Further, the large electronic parts 24a and 24b are mounted apart from the large electronic part 50 on the mounting faces of the illumination board section 20R1 and the imaging board section 20R2 that oppose to each other, so that the exterior dimension in an elongated direction of the capsule endoscope C can be miniaturized. Further, the rigid wiring board sections 20R are bonded with each other by the electrically insulated resin sealant P, thus it is easy to handle the rigid and flexible wiring board section. Consequently, short circuit of the electronic parts can be avoided without insulation of the electronic parts by a separate insulating film and the like, since the resin sealant P is insulated. Therefore, assembly operation does not become complicated.

The sealed container 100 that houses the button cell 10 and the rigid and flexible wiring board 20 is provided with a container main body 110 and a front cover 120, which separately constitute the sealed container 100.

Figure 18:
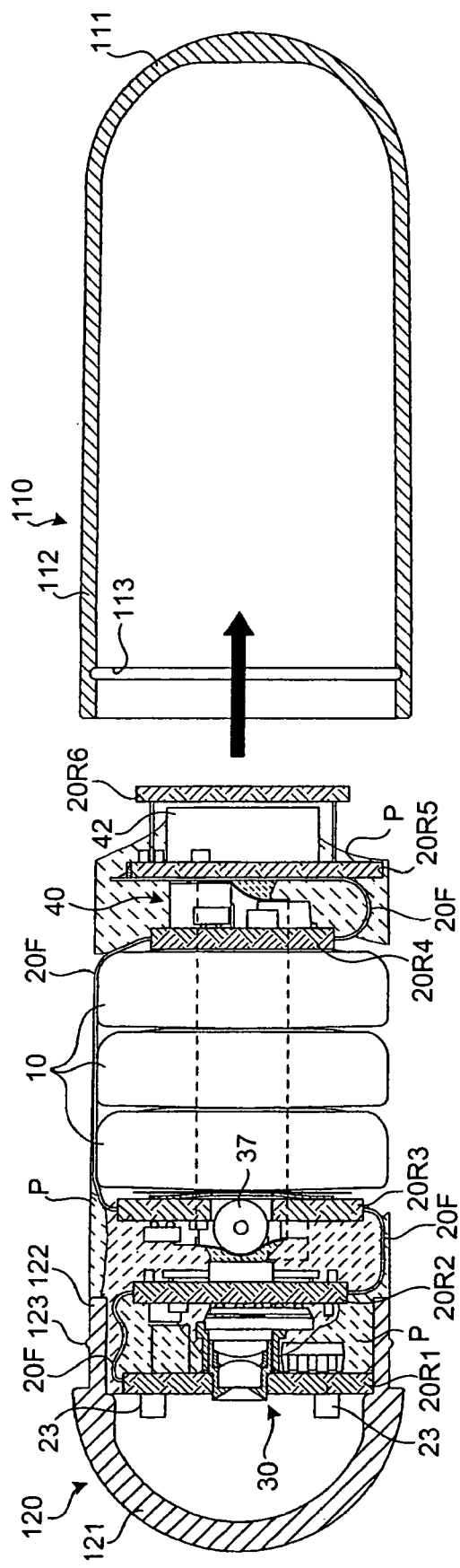
FIG. 18 is an exploded sectional side view showing a state in which the internal member of the capsule endoscope shown in FIG. 1 is inserted into a sealed container.

The container main body 110 has substantially semi spherical dome-shaped bottom portion 111 and a substantially cylindrical barrel portion 112 that extends to the bottom portion 111 as shown in FIGS. 1 and 18, and the bottom portion 111 and the barrel portion 112 are integrally molded by synthetic resin material. Cycloolefin polymer, polycarbonate, acrylic, polysulfone, and urethane, for example, can be used as the synthetic resin material for molding the container main body 110; however, the polysulfone is preferably used when strength of the container main body 110 is considered.

The barrel portion 112 of the container main body 110 has a predetermined draft, and a diameter of the barrel portion 112 gradually increases towards an opening at the distal end thereof, though not clearly shown in the drawings. A dimension of the container main body 110 is set so that the rigid and flexible wiring board section 20, which is blocked as the interior member, and the button cell 10 can be housed in the container main body 110 when the rigid and flexible wiring board section 20 and the button cell 10 are inserted from the antenna board section 20R6 side as shown in FIG. 1. Further, the dimension of the container main body 110 is set so that a space between the container main body 110 and the housed interior member is minimized.

An engagement groove 113 is formed around entire periphery of an internal periphery face of the barrel portion 112 of the container main body 110 at a position slightly towards a proximal end from the opening at the distal end.

The front cover 120 has a substantially semi spherical dome-shaped dome portion 121 and an engagement portion 122 that cylindrically extends from a proximal end of the dome portion 121 as shown in FIG. 1, and the dome portion 121 and the engagement portion 122 are integrally molded by the synthetic resin material, which is to be an optical material. Cycloolefin polymer, polycarbonate, acrylic, polysulfone, and urethane can be used as the synthetic resin material for modulating the front cover 120; however, the cycloolefin polymer or the polycarbonate is preferably used when strength and optical performance of the front cover 120 are considered.

The dome portion 121 of the front cover 120 has an exterior dimension substantially the same as an exterior dimension of the distal end of the barrel portion 112 of the container main body 110. Further, the engagement portion 122 has an exterior dimension capable of fitting into the interior periphery of the distal end of the barrel portion 112 of the container main body 110. Therefore, the front cover 120 can be fitted into the interior periphery of the distal end of the barrel portion 112 through the engagement portion 122 in a way so that an exterior face of the dome portion 121 smoothly continues to an exterior face of the barrel portion 112, when the front cover 120 is attached to the distal end of the container main body 110.

An engagement protrusion 123 is provided at entire circumference of the engagement portion 122 of the front cover 120. Here, the engagement protrusion 123 corresponds to the engagement groove 113 of the container main body 110. The engagement protrusion 123 is provided to prevent unnecessary fall out of the front cover 120 from the container main body 110, by engaging the engagement protrusion 123 to the engagement groove 113 of the container main body 110 when the front cover 120 is attached to the distal end of the barrel portion 112. Further, the engagement portion 122 has an interior diameter capable of fitting the illumination board section 20R1 of the rigid and flexible wiring board section 20 therein.

A translucent portion 121a is provided at a region, which is a predetermined symmetric region having a center at center of curvature of the dome portion 121 (inside a region surrounded by two points chained line in FIG. 1). Further, a pupil portion 121b is provided at entire periphery positioned closer to the container main body 110 compared to the position of the translucent portion 121a.

The translucent portion 121a and the pupil portion 121b are sections to determine the observed region of the image data with respect to the front cover 120. The translucent portion 121a of the front cover 120 is formed to have homogeneity and uniform thickness. On the other hand, the pupil portion 121b is formed to be thicker than the translucent portion 121a, and the pupil portion 121b has a projection portion 124 that swells out inwards from the interior periphery face of the engagement portion 122. A abutting surface 125, which is positioned at a proximal end side of the projection portion 124, extends in a direction orthogonal to a center of axis of the front cover 120. The projection portion 124 is configured so that the optical axis of the lens unit 30 matches the center of axis of the front cover 120 as well as a center of the entrance pupil with respect to the lens unit 30 matches the center of the curvature of the front cover 120 (=center of the entrance pupil of the front cover 120) on the optical axis, when one of the mounting faces of the illumination board section 20R1 contacts and engages to the projection portion 124. An interior diameter of the projection portion 124 is larger than a mounting region of the light-emitting device 23 mounted on the illumination board section 20R1 so that the projection portion 124 does not interfere with the light-emitting device 23 when the illumination board section 20R1 is rotated with respect to the center of axis of the illumination board section 20R1.

When the blocked rigid and flexible wiring board section 20 and the button cell 10 are to be housed in the sealed container 100 described above, the illumination board section 20R1 is covered by the front cover 120 in advance as shown in FIG. 18. Then, the bonding agent is applied to the interior periphery face of the container main body 110, as well as the electrically insulated resin sealant P is applied around the rigid and flexible wiring board section 20 and the button cell 10. The internal member is inserted into the container main body 110 after applying the resin sealant P, and the engagement protrusion 123 of the front cover 120 is engaged to the engagement groove 113 of the container main body 110. When the engagement protrusion 123 of the front cover 120 is engaged to the engagement groove 113 of the container main body 110, the front cover 120 and the container main body 110 are preferably rotated relative to each other in order to send the bonding agent around the entire periphery thereof.

As described above, the optical axis of the lens unit 30 matches the center of axis of the front cover 120 without being tilted and the center of the entrance pupil of the lens unit 30 matches the center of curvature of the front cover 120, when one of the mounting faces of the illumination board section 20R1 is contacted and engaged to the abutting surface 125 of the front cover 120. Further, the projection portion 124 of the front cover 120 does not interfere with the light-emitting device 23 of the illumination board section 20R1 when the illumination board section 20R1 is inserted into the engagement portion 122. Consequently, it is unnecessary to consider the relative position of the illumination board section 20R1 and the front cover 120. Further, it is unnecessary to adjust the position of the optical system with respect to the incident light while assembling the capsule endoscope C, and the assembly operation can be easily performed.

The bonding agent infiltrated between the interior periphery face of the container main body 110 and the exterior periphery face of the engagement portion 122 at the front cover 120 provides desired water-tightness therebetween. Consequently, liquid such as body fluid does not infiltrate into the sealed container 100 when the capsule endoscope C is inserted into the body cavity. Specifically, the bonding agent between the front cover 120 and the container main body 110 is not abraded after sterilization and the like after the assembly operation, since the engagement protrusion 123 and the engagement groove 113 are engaged to each other. Consequently, breakdown of the internal member due to the infiltration of the body fluid can be avoided.

A connection section, which appears on the exterior surface of the sealed container 100, between the front cover 120 and the container main body 110 when the front cover 120 and the container main body 110 are connected to each other is chamfered as shown in the drawings. Consequently, it is possible to prevent occurrence of external force in the direction separating the front cover 120 and the container main body 110 due to the front cover 120 and the container main body 110 being caught, because the chamfer processing minimizes a bump caused between the front cover 120 and the container main body 110. Therefore, the water-tightness of the sealed container 100 is assured.

Figure 19:
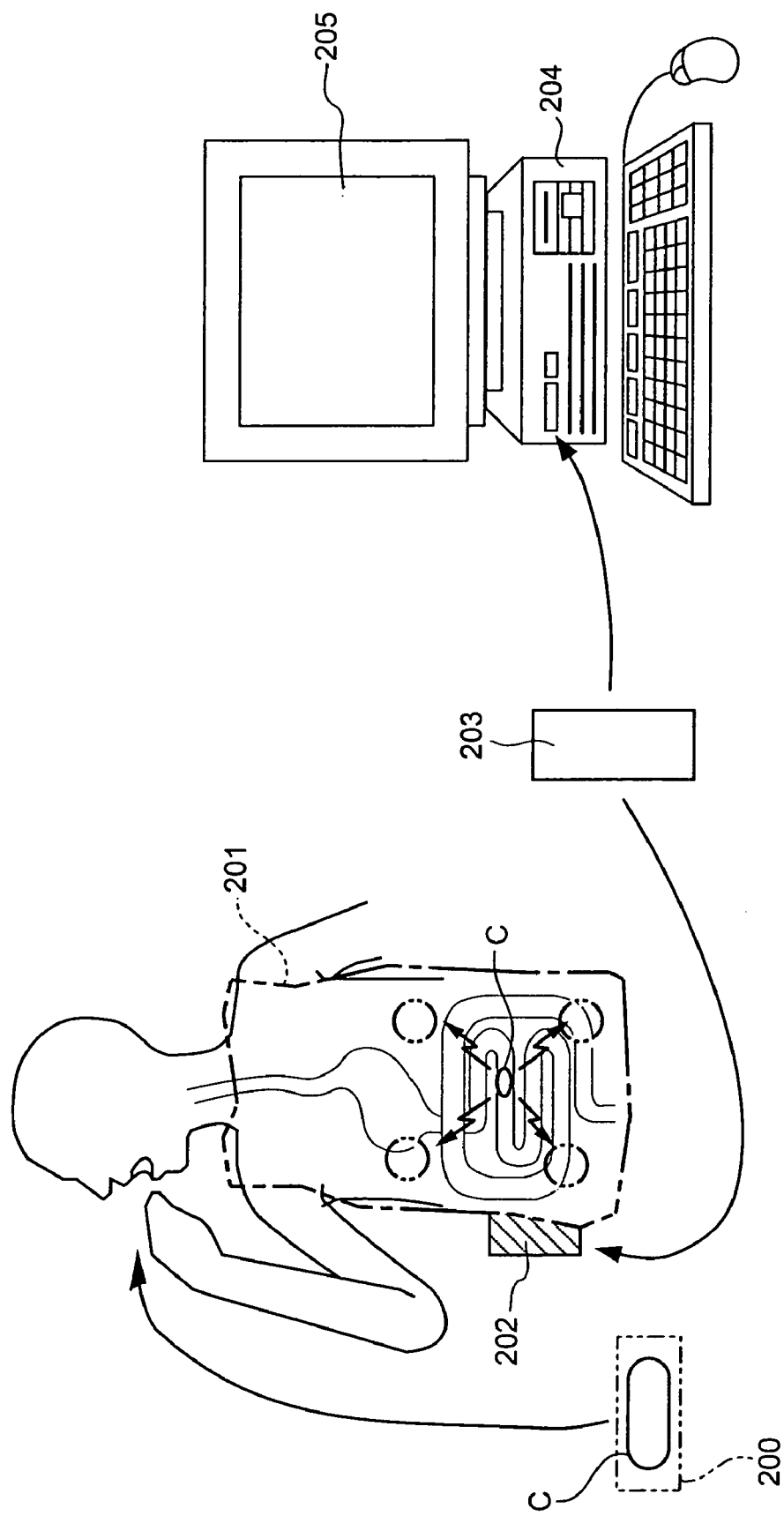
FIG. 19 is a schematic drawing showing an example of use of the capsule endoscope.
Figure 20:
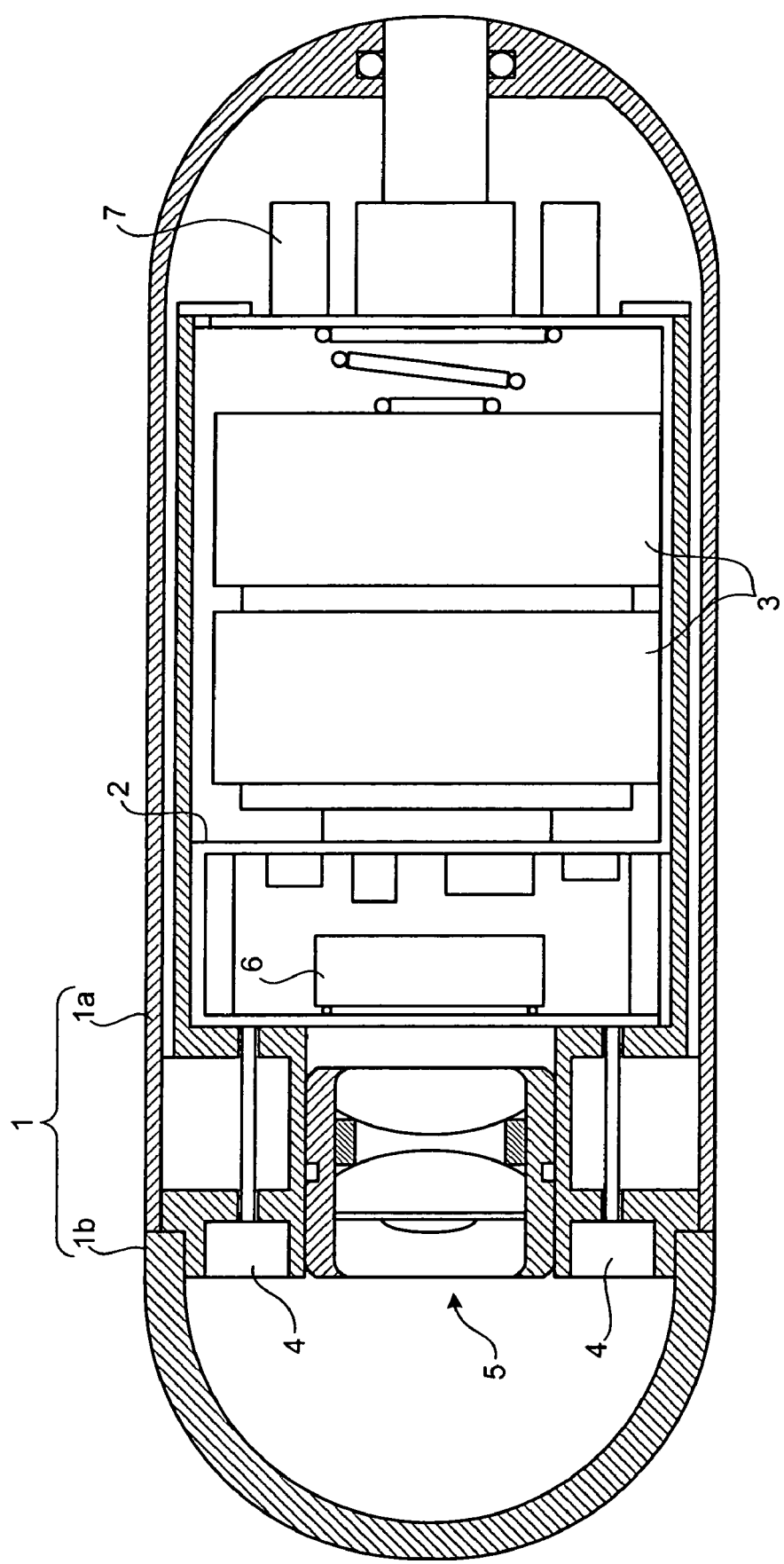
FIG. 20 is a sectional side view showing a conventional capsule endoscope.
Figure 21:
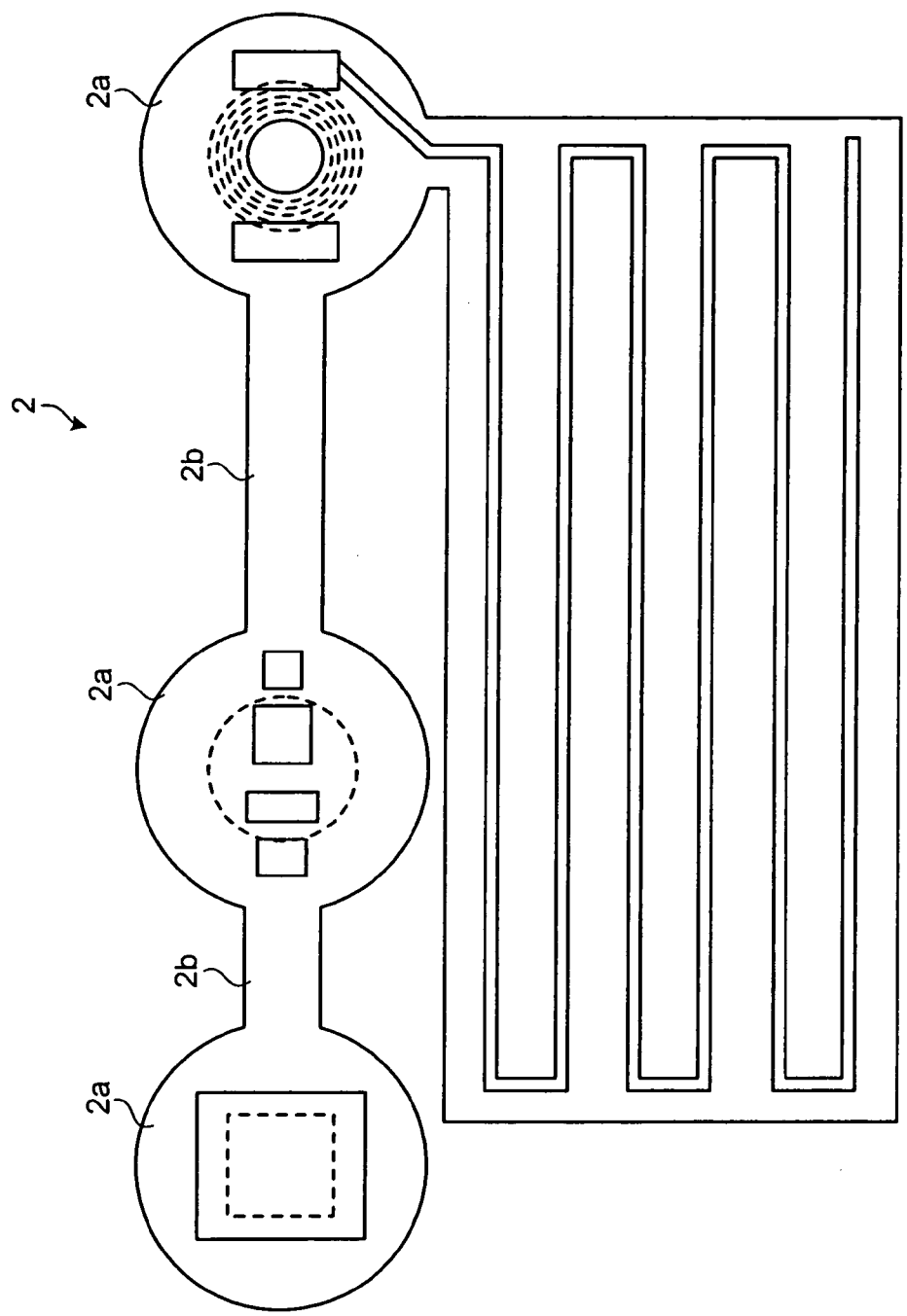
FIG. 21 is a development plan view of the wiring board section used for the capsule endoscope shown in FIG. 20.

FIG. 19 is a schematic drawing for explaining an example of use of the capsule endoscope C described above. In the following, an operation of the capsule endoscope C is explained with reference to FIG. 19.

First, the reed switch 37 is activated by taking out the capsule endoscope C of the present embodiment from a package 200 in which the permanent magnet (not shown) is built, and the electrical power for the functional circuit from the button cell 10, which is the internal power supply, is continuously supplied through the DC-DC converter 40.

When the subject wearing a jacket 201 swallows the capsule endoscope C while the electric power is supplied, each part of the functional circuit is driven by an order from the DSP 25, so that the image data of the subject body can be acquired until the capsule endoscope C is discharged. More particularly, the light-emitting device 23 illuminates the observed region of the subject body such as stomach, small intestine, and large intestine with the illuminating light through the translucent portion 121a of the front cover 120. Further, the reflected light entering through the Translucent portion 121a of the front cover 120 is assembled on the CCD 26 through the lens unit 30. Then, the reflected light assembled on the CCD 26 is outputted as the image signal.

The image signal output from the CCD 26 is radio transmitted to outside from the antenna 43 after the image signal is modulated and amplified in the RF unit 42. Then, the image signal is sequentially stored as the image data into an external memory device 203, such as a Compactflash® memory, of the receiver 202 attached to the jacket 201. The image data stored in the external memory device 203 is, for example, visualized on a display 205 through a computer 204 so that the viewable image data becomes a subject of diagnosis by a doctor or a nurse.

In the capsule endoscope C described above, the rigid and flexible wiring board 20 in which each of the straight-line portions 22R of the plurality of comparatively rigid wiring board sections 20R is connected to each other through the comparatively flexible wiring board section 20F. Consequently, it is possible to easily and accurately bend the flexible wiring board section 20F at the steady position near the straight-line portion 22R of the rigid wiring board section 20R when the rigid and flexible printed circuit board 20 is cylindrically blocked to be housed inside the sealed container 100. Therefore, the exterior dimension of the blocked rigid and flexible wiring board 20 does not become larger than the interior diameter of the sealed container 100, so that the rigid and flexible wiring board section 20 can be easily housed inside the sealed container 100.

Further, the straight-line portion R22 of each of the rigid wiring board sections 20R is formed by removing the penumbra thereof, thus the space 20FK between the straight-line portion 22R and the container main body 110 for housing the flexible circuit board section 20F is formed as shown in FIGS. 5 to 9. Furthermore, the flexible wiring board section 20F arranged at the exterior periphery section of the button cell 10 is divided into two by the slit 20FS formed along the elongated direction of the flexible wiring board section 20F. Consequently, the flexible wiring board section 20F is placed close to the periphery face of the button cell 10, and it becomes possible to minimize the exterior dimension of the cylindrically blocked interior member as well as to minimize the exterior dimension of the sealed container 100 that houses the interior member. Hence, suffering by the subject when the capsule endoscope C is swallowed can be reduced as far as possible.

Further, the diameter of the antenna board section 20R6, which is the first board section to be inserted into the sealed container 100 among the board sections of the rigid wiring board section 20R, is the smallest of all so that the rigid wiring board section 20R can be easily inserted into the container main body 110 of the sealed container 100.

The flexible wiring board section 20F arranged at the external periphery of the button cell 10 is divided into two by the slit 20FS formed along the elongated direction thereof in the embodiment described above; however, it is not required to divide the flexible wiring board section 20F into two in the present invention. Thus, the flexible wiring board section 20F can be divided into three or more.

The embodiment described above has a relationship in which (the exterior diameter of the illumination board section 20R1)>(the exterior diameter of the imaging board section 20R2)>(the exterior diameter of the switch board section 20R3)>(the exterior diameter of the power supply board section 20R4)>(the exterior diameter of the transmission board section 20R5)>(the exterior diameter of the antenna board section 20R6). Therefore, the bonding agent applied to the interior periphery face of the container main body 110 cannot be wiped out by the rigid wiring board section 20R of the distal end side when the rigid wiring board section 20R is inserted into the container main body 110. Consequently, it is possible to maintain sufficient bonding property with respect to the container main body 110. In the present invention, it suffices to set the exterior diameter of the antenna board section 20R6 smaller than the exterior diameter of the transmission board section 20R5 that is arranged right in front of the antenna board section 20R6.

The embodiment described above is explained in terms of the capsule endoscope C by way of example; however, the present invention can be applied to other capsule-type medical apparatus such as a pH capsule and a temperature measuring capsule.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule-type medical apparatus, comprising:
    a sealed container; and
    a wiring board which is housed in the sealed container and on which a functional circuit performing a predetermined function while the capsule-type medical apparatus is inserted into a subject is mounted, the wiring board including
        a plurality of comparatively rigid wiring board sections on which parts constituting the functional circuit are mounted, the rigid wiring board sections being disk-shaped, and
        a comparatively flexible wiring board section that connects the plurality of the rigid wiring board sections in series, wherein
    each of the rigid wiring board sections include, along a periphery, a straight-line portion provided orthogonally with respect to an extending direction of the flexible wiring board section, and
    the flexible wiring board section is folded along the straight-line portion so that the adjacent rigid wiring board sections oppose to each other.

2. The capsule-type medical apparatus according to claim 1, wherein
    an interior of the sealed container has a circular cross-section, and
    each straight-line portion is formed by removing a section of the rigid wiring board section from which the flexible wiring board section is extended.

3. The capsule-type medical apparatus according to claim 2, wherein
    the rigid wiring board section has a dimension such that the rigid wiring board section fits inside the sealed container, and
    a space for arranging the flexible wiring board section is formed between the sealed container and the straight-line portion.

4. An capsule-type medical apparatus, comprising:
    a sealed container; and
    a wiring board which is housed in the sealed container and on which a functional circuit performing a predetermined function while the capsule-type medical apparatus is inserted into a subject is mounted, the wiring board including
        a plurality of rigid wiring board sections on which parts constituting the functional circuit are mounted, the rigid wiring board sections being disk-shaped, and
        a flexible wiring board section that connects the plurality of the rigid wiring board sections in series so that the adjacent rigid wiring board sections oppose to each other, wherein
    each of the rigid wiring board sections include, along a periphery, a straight-line portion provided orthogonally with respect to an extending direction of the flexible wiring board section,
    the flexible wiring board section is folded along the straight-line portion so that the adjacent rigid wiring board sections oppose each other, and
    parts with a protruding height that exceeds a predetermined threshold being mounted on the rigid wiring board sections that oppose to each other at such positions that the parts do not oppose to each other.

5. The capsule-type medical apparatus according to claim 4, wherein the opposing rigid wiring board sections are bonded by a resin sealant before the rigid wiring board sections are housed in the sealed container.

6. The capsule-type medical apparatus according to claim 5, wherein the resin sealant has an electrical insulating property.

* * * * *